(12) United States Patent
Wang

(10) Patent No.: US 11,684,417 B2
(45) Date of Patent: *Jun. 27, 2023

(54) CHEMICAL ABLATION FORMULATIONS AND METHODS OF TREATMENTS FOR VARIOUS DISEASES

(71) Applicant: Neurotronic, Inc., Plymouth, MN (US)

(72) Inventor: Lixiao Wang, Henderson, NV (US)

(73) Assignee: Neurotronic, Inc., Plymouth, MN (US)

(*) Notice: Subject to any disclaimer, the term of this patent is extended or adjusted under 35 U.S.C. 154(b) by 950 days.

This patent is subject to a terminal disclaimer.

(21) Appl. No.: 16/563,192

(22) Filed: Sep. 6, 2019

(65) Prior Publication Data
US 2019/0388147 A1 Dec. 26, 2019

Related U.S. Application Data

(63) Continuation of application No. 16/419,587, filed on May 22, 2019, now Pat. No. 11,382,689, which is a
(Continued)

(51) Int. Cl.
*A61B 18/14* (2006.01)
*A61B 18/02* (2006.01)
(Continued)

(52) U.S. Cl.
CPC ...... *A61B 18/1492* (2013.01); *A61B 18/0218* (2013.01); *A61B 18/18* (2013.01);
(Continued)

(58) Field of Classification Search
CPC ............ A61M 25/10; A61M 2025/105; A61B 18/0218; A61B 2018/0212; A61B 2018/00577
See application file for complete search history.

(56) References Cited

U.S. PATENT DOCUMENTS 4,254,056 A * 3/1981 Konno .................... A61P 29/00
564/387
4,573,966 A 3/1986 Weikl et al.
(Continued)

FOREIGN PATENT DOCUMENTS

CN 1593359 A 3/2005
CN 101861184 A 10/2010
(Continued)

OTHER PUBLICATIONS

"U.S. Appl. No. 16/419,587, Non Final Office Action dated Oct. 5, 2021", 15 pgs.
(Continued)

*Primary Examiner* — Nathan R Price
*Assistant Examiner* — Anh Bui
(74) *Attorney, Agent, or Firm* — Schwegman, Lundberg & Woessner, P.A.

(57) ABSTRACT

Embodiments of the present invention are directed to the treatment of hypertension, diabetes, obesity, heart failure, end-stage renal disease, digestive disease, urological disease, cancers, tumors, pains, asthma, pulmonary arterial hypertension, and chronic obstructive pulmonary disease by delivering of an effective amount of formulations at desired temperature to target tissue. The formulations include gases, vapors, liquids, solutions, emulsions and suspensions of one or more ingredients. The temperature may enhance safety and efficacy of the formulations for the treatments. The amounts of the formulation and/or energy are effective to injury or damage the tissues to have a benefit of symptom relive.

25 Claims, 6 Drawing Sheets

Related U.S. Application Data continuation of application No. 14/438,411, filed as application No. PCT/US2013/067382 on Oct. 30, 2013, now abandoned.

(60) Provisional application No. 61/849,928, filed on Feb. 5, 2013, provisional application No. 61/848,483, filed on Jan. 4, 2013, provisional application No. 61/797,647, filed on Dec. 12, 2012, provisional application No. 61/796,118, filed on Nov. 2, 2012.

(51) Int. Cl.

| | |
|---|---|
| *A61B 18/18* | (2006.01) |
| *A61B 18/24* | (2006.01) |
| *A61K 49/04* | (2006.01) |
| *A61M 25/10* | (2013.01) |
| *A61N 7/00* | (2006.01) |
| *A61B 18/00* | (2006.01) |
| *A61F 7/12* | (2006.01) |
| *A61K 47/12* | (2006.01) |
| *A61K 47/10* | (2017.01) |
| *A61F 7/00* | (2006.01) |
| *A61K 47/14* | (2017.01) |

(52) U.S. Cl.
CPC .......... *A61B 18/1815* (2013.01); *A61B 18/24* (2013.01); *A61K 49/0438* (2013.01); *A61M 25/10* (2013.01); *A61N 7/00* (2013.01); *A61B 2018/00285* (2013.01); *A61B 2018/00345* (2013.01); *A61B 2018/00482* (2013.01); *A61B 2018/00541* (2013.01); *A61B 2018/00577* (2013.01); *A61B 2018/00994* (2013.01); *A61B 2018/0212* (2013.01); *A61F 2007/0063* (2013.01); *A61F 2007/0091* (2013.01); *A61F 2007/126* (2013.01); *A61K 47/10* (2013.01); *A61K 47/12* (2013.01); *A61K 47/14* (2013.01); *A61M 25/1011* (2013.01); *A61M 2025/1052* (2013.01); *A61N 2007/0043* (2013.01)

(56) References Cited

U.S. PATENT DOCUMENTS

| | | | |
|---|---|---|---|
| 4,653,438 A | 3/1987 | Russell | |
| 5,263,931 A | 11/1993 | Miller | |
| 5,314,443 A | 5/1994 | Rudnick | |
| 5,315,992 A | 5/1994 | Dalton | |
| 5,380,284 A | 1/1995 | Don | |
| 5,419,763 A | 5/1995 | Hildebrand | |
| 5,423,755 A | 6/1995 | Kesten et al. | |
| 5,460,610 A | 10/1995 | Don | |
| 5,599,307 A * | 2/1997 | Bacher | A61M 25/104 |
| | | | 604/509 |
| 5,681,281 A | 10/1997 | Vigil et al. | |
| 5,720,735 A | 2/1998 | Dorros | |
| 6,048,332 A | 4/2000 | Duffy et al. | |
| 6,062,223 A | 5/2000 | Palazzo et al. | |
| 6,135,981 A | 10/2000 | Dyke | |
| 6,258,087 B1 | 7/2001 | Edwards et al. | |
| 6,623,452 B2 | 9/2003 | Chien et al. | |
| 6,685,672 B1 | 2/2004 | Forman | |
| 7,617,005 B2 | 11/2009 | Demarais et al. | |
| 7,653,438 B2 | 1/2010 | Deem et al. | |
| 7,717,948 B2 | 5/2010 | Demarais et al. | |
| 8,052,668 B2 | 11/2011 | Sih | |
| 8,372,054 B2 | 2/2013 | Duffy et al. | |
| 8,774,913 B2 | 7/2014 | Demarais et al. | |
| 8,840,601 B2 | 9/2014 | Salahieh et al. | |
| 9,114,123 B2 | 8/2015 | Vafai et al. | |
| 10,286,191 B2 | 5/2019 | Wang et al. | |
| 10,537,375 B2 | 1/2020 | Wang | |
| 10,758,713 B2 | 9/2020 | Wang et al. | |
| 11,382,689 B2 * | 7/2022 | Wang | A61B 18/04 |
| 11,517,725 B2 | 12/2022 | Wang et al. | |
| 2002/0014238 A1 | 2/2002 | Kotmel | |
| 2002/0068953 A1 | 6/2002 | Kokish | |
| 2002/0177846 A1 | 11/2002 | Mulier | |
| 2003/0066532 A1 | 4/2003 | Gobel | |
| 2004/0267336 A1 | 12/2004 | Morrison et al. | |
| 2005/0288639 A1 * | 12/2005 | Hibner | A61M 25/04 |
| | | | 600/29 |
| 2006/0161233 A1 | 7/2006 | Barry et al. | |
| 2006/0265014 A1 | 11/2006 | Demarais et al. | |
| 2006/0282120 A1 | 12/2006 | Sih | |
| 2007/0077230 A1 | 4/2007 | Mon | |
| 2008/0114297 A1 | 5/2008 | Barry et al. | |
| 2008/0118544 A1 | 5/2008 | Wang | |
| 2008/0208118 A1 | 8/2008 | Goldman | |
| 2008/0255508 A1 | 10/2008 | Wang | |
| 2008/0255509 A1 | 10/2008 | Wang | |
| 2009/0192505 A1 | 7/2009 | Askew et al. | |
| 2009/0301483 A1 | 12/2009 | Barry et al. | |
| 2010/0010470 A1 | 1/2010 | Bates | |
| 2010/0145304 A1 | 6/2010 | Cressman | |
| 2010/0209472 A1 | 8/2010 | Wang | |
| 2011/0104061 A1 | 5/2011 | Seward | |
| 2011/0152683 A1 | 6/2011 | Gerrans et al. | |
| 2011/0182912 A1 * | 7/2011 | Evans | A61K 31/198 |
| | | | 514/17.7 |
| 2011/0218564 A1 | 9/2011 | Drasler et al. | |
| 2012/0083809 A1 | 4/2012 | Drasler et al. | |
| 2012/0116438 A1 | 5/2012 | Salahieh et al. | |
| 2012/0197245 A1 | 8/2012 | Burnett et al. | |
| 2012/0209251 A1 | 8/2012 | Bates | |
| 2012/0215212 A1 | 8/2012 | Selzer et al. | |
| 2012/0259269 A1 | 10/2012 | Meyer | |
| 2012/0271277 A1 | 10/2012 | Fischell et al. | |
| 2012/0271301 A1 | 10/2012 | Fischell et al. | |
| 2013/0189190 A1 | 7/2013 | Wang | |
| 2015/0056298 A1 * | 2/2015 | Azamian | A61B 18/02 |
| | | | 514/183 |
| 2015/0272666 A1 | 10/2015 | Wang | |
| 2016/0135879 A1 * | 5/2016 | Beasley | A61M 25/0023 |
| | | | 606/41 |
| 2016/0310200 A1 | 10/2016 | Wang | |
| 2018/0015264 A1 | 1/2018 | Wang et al. | |
| 2019/0038881 A1 | 2/2019 | Wang et al. | |
| 2019/0307507 A1 | 10/2019 | Wang | |
| 2020/0009355 A1 | 1/2020 | Wang et al. | |
| 2020/0016379 A1 | 1/2020 | Wang et al. | |
| 2020/0086093 A1 | 3/2020 | Wang | |
| 2020/0360671 A1 | 11/2020 | Wang et al. | |
| 2020/0398032 A1 | 12/2020 | Wang et al. | |
| 2021/0275784 A1 | 9/2021 | Wang | |
| 2021/0275785 A1 | 9/2021 | Wang | |
| 2021/0275786 A1 | 9/2021 | Wang | |
| 2021/0275787 A1 | 9/2021 | Wang | |
| 2022/0233827 A1 | 7/2022 | Wang et al. | |

FOREIGN PATENT DOCUMENTS

| | | |
|---|---|---|
| CN | 102481428 | 5/2012 |
| CN | 102600546 A | 7/2012 |
| CN | 102698354 | 10/2012 |
| CN | 102727986 A | 10/2012 |
| CN | 102743163 A | 10/2012 |
| CN | 107106820 A | 8/2017 |
| CN | 110772311 | 2/2020 |
| CN | 113040895 | 6/2021 |
| EP | 2497524 A1 | 9/2012 |
| JP | H04215767 | 8/1992 |
| JP | H07308382 | 11/1995 |
| JP | 08508917 A | 9/1996 |
| JP | 2000279524 | 10/2000 |
| JP | 2004180892 A | 7/2004 |
| JP | 2004528924 A | 9/2004 |
| JP | 2005506101 A | 3/2005 |
| JP | 2006502801 | 1/2006 |
| JP | 2010078379 A | 4/2010 |
| JP | 2010519005 A | 6/2010 |

(56) References Cited

FOREIGN PATENT DOCUMENTS

| | | |
|---|---|---|
| JP | 2010528815 A | 8/2010 |
| JP | 2011519699 A | 7/2011 |
| JP | 2012505050 | 3/2012 |
| JP | 2012508067 A | 4/2012 |
| JP | 2012517858 A | 8/2012 |
| JP | 2012524808 | 10/2012 |
| JP | 2013517847 | 5/2013 |
| JP | 2014524342 A | 9/2014 |
| JP | 2014527272 | 10/2014 |
| JP | 2015536945 | 12/2015 |
| JP | 2017533036 A | 11/2017 |
| JP | 6389185 B2 | 8/2018 |
| JP | 2020189858 | 11/2020 |
| JP | 2021046397 | 3/2021 |
| WO | WO-9421320 A1 | 9/1994 |
| WO | WO-9618427 A1 | 6/1996 |
| WO | WO-9717099 A1 | 5/1997 |
| WO | WO-0119445 A1 | 3/2001 |
| WO | 02051490 | 7/2002 |
| WO | WO-2006055695 A1 | 5/2006 |
| WO | 2008106357 | 9/2008 |
| WO | WO-2009076732 A1 | 6/2009 |
| WO | WO-2009082433 A2 | 7/2009 |
| WO | WO-2010033686 A1 | 3/2010 |
| WO | 2010124120 | 10/2010 |
| WO | 2011094367 | 8/2011 |
| WO | WO-2011119159 A1 | 9/2011 |
| WO | 2013026565 | 2/2013 |
| WO | WO-2013028781 A1 | 2/2013 |
| WO | 2013067382 | 5/2013 |
| WO | WO-201 3090848 A1 | 6/2013 |
| WO | WO-201 4070820 A2 | 5/2014 |
| WO | 2015058296 | 4/2015 |
| WO | WO-2016070032 A1 | 5/2016 |

OTHER PUBLICATIONS

"Effectiveness and Safety of Bronchial Thermoplasty in the Treatment of Severe Asthma", A Multicenter, Randomized, Double-Blind, Sham-Controlled Clinical Trial Am J Respir Crit Care Med vol. 181., (2010), 9 pgs.
"U.S. Appl. No. 16/419,587, Response filed Nov. 4, 2021 to Non Final Office Action dated Oct. 5, 2021", 12 pgs.
"U.S. Appl. No. 16/563,235, Response filed Nov. 16, 2021 to Non Final Office Action dated Sep. 30, 2021", 13 pgs.
"Japanese Application Serial No. 2018-153239, Response filed Nov. 16, 21 to Notification of Reasons for Refusal dated Aug. 17, 2021", w Engilsh Claims, 10 pgs.
"Japanese Application Serial No. 2018-153239, Notification of Reasons for Refusal dated Jan. 5, 2022", w English Translation, 17 pgs.
"Japanese Application Serial No. 2020-178075, Notification of Reasons for Refusal dated Jan. 5, 2022", w English Translation, 8 pgs.
Dunican, Eleanor M, "Mucus plugs in patients with asthma linked to eosinophilia and airflow obstruction", J Clin Invest. 2018;128(3), (2018), 14 pgs.
Greer, M, "Paclitaxel-Coated Balloons in Refractory Nonanastomotic Airway Stenosis Following Lung Transplantation", American Journal of Transplantation 2014 14: 2400-2405, (2014), 2400-2405.
Kim, K. C., "Airway goblet cell mucin: its structure and regulation of secretion", Series Airway Mucus Eur Respir J 1997; 10:, (1997), pp. 2644-2649.
Krmisky, William, "Thermal ablation for asthma: current status and technique", J Thorac Dis 2017;9(Suppl 2):S104-S109, (2017), 6 pgs.
Menzella, Francesco, "Anti-IL5 Therapies for Severe Eosinophilic Asthma: Literature Review and Practical Insights", Journal of Asthma and Allergy 2020:13, (2020), 13 pgs.
Petters, Michael C, "Evidence for Exacerbation-Prone Asthma and Predictive Biomarkers of Exacerbation Frequency", Am J Respir Crit Care Med vol. 202, Iss 7, (2020), 10 pgs.
Sakata, Kenneth K, "Paclitaxel-coated balloon dilation for central airway obstruction", Respiratory Medicine Case Reports 24, (2018), 129-132.
"U.S. Appl. No. 14/438,411, Advisory Action dated Apr. 30, 2019", 3 pgs.
"U.S. Appl. No. 14/438,411, Final Office Action dated Feb. 25, 2019", 15 pgs.
"U.S. Appl. No. 14/438,411, Final Office Action dated May 9, 2018", 9 pgs.
"U.S. Appl. No. 14/438,411, Non Final Office Action dated Sep. 21, 2018", 11 pgs.
"U.S. Appl. No. 14/438,411, Non Final Office Action dated Oct. 20, 2017", 9 pgs.
"U.S. Appl. No. 14/438,411, Preliminary Amendment filed Jul. 28, 2015", 9 pgs.
"U.S. Appl. No. 14/438,411, Response filed Jan. 17, 2018 to Non Final Office Action dated Oct. 20, 2017", 9 pgs.
"U.S. Appl. No. 14/438,411, Response filed Apr. 16, 2019 to Final Office Action dated Feb. 25, 2019", 18 pgs.
"U.S. Appl. No. 14/438,411, Response filed Aug. 7, 2018 to Final Office Action dated May 9, 2018", 12 pgs.
"U.S. Appl. No. 14/438,411, Response filed Aug. 25, 2017 to Restriction Requirement dated Jul. 14, 2017", 7 pgs.
"U.S. Appl. No. 14/438,411, Response filed Oct. 8, 2018 to Non Final Office Action dated Sep. 21, 2018", 17 pgs.
"U.S. Appl. No. 14/438,411, Restriction Requirement dated Jul. 14, 2017", 8 pgs.
"U.S. Appl. No. 15/133,976, Advisory Action dated Jul. 30, 2019", 7 pgs.
"U.S. Appl. No. 15/133,976, Final Office Action dated May 3, 2019", 15 pgs.
"U.S. Appl. No. 15/133,976, Final Office Action dated Aug. 16, 2018", 26 pgs.
"U.S. Appl. No. 15/133,976, Non Final Office Action dated Feb. 15, 2018", 16 pgs.
"U.S. Appl. No. 15/133,976, Non Final Office Action dated Nov. 30, 2018", 14 pgs.
"U.S. Appl. No. 15/133,976, Preliminary Amendment filed Apr. 20, 2016", 7 pgs.
"U.S. Appl. No. 15/133,976, Response filed Mar. 20, 2019 to Non Final Office Action dated Nov. 30, 2018", 17 pgs.
"U.S. Appl. No. 15/133,976, Response filed Jun. 14, 2018 to Non Final Office Action dated Feb. 15, 2018", 13 pgs.
"U.S. Appl. No. 15/133,976, Response filed Jul. 1, 2019 to Final Office Action dated May 3, 2019", 20 pgs.
"U.S. Appl. No. 15/133,976, Response filed Oct. 26, 2018 to Final Office Action dated Aug. 16, 2018", 20 pgs.
"U.S. Appl. No. 15/133,976, Response filed Dec. 27, 2017 to Restriction Requirement dated Oct. 31, 2017", 8 pgs.
"U.S. Appl. No. 15/133,976, Restriction Requirement dated Oct. 31, 2017", 7 pgs.
"U.S. Appl. No. 15/521,973, Examiner Interview Summary dated Jun. 4, 2018", 3 pgs.
"U.S. Appl. No. 15/521,973, Final Office Action dated Jan. 15, 2019", 16 pgs.
"U.S. Appl. No. 15/521,973, Non Final Office Action dated May 18, 2018", 21 pgs.
"U.S. Appl. No. 15/521,973, Non Final Office Action dated Sep. 14, 2018", 15 pgs.
"U.S. Appl. No. 15/521,973, Notice of Allowance dated Mar. 27, 2019", 7 pgs.
"U.S. Appl. No. 15/521,973, Preliminary Amendment filed Apr. 26, 2017", 8 pgs.
"U.S. Appl. No. 15/521,973, Response filed Mar. 14, 2019 to Final Office Action dated Jan. 15, 2019", 16 pgs.
"U.S. Appl. No. 15/521,973, Response filed Dec. 10, 2018 to Non Final Office Action dated Sep. 14, 2018", 11 pgs.
"U.S. Appl. No. 16/419,587, Preliminary Amendment filed Jul. 9, 19", 3 pgs.
"Chinese Application Serial No. 201380055918.X, Office Action dated Jan. 17, 2018", (English Translation), 8 pgs.
"Chinese Application Serial No. 201380055918.X, Office Action dated Feb. 19, 2017", w/ English Translation, 6 pgs.

(56) References Cited

OTHER PUBLICATIONS

"Chinese Application Serial No. 201380055918.X, Office Action dated May 19, 2017", w/ English Translation, 18 pgs.
"Chinese Application Serial No. 201380055918.X, Response filed Apr. 2, 2018 to Office Action dated Jan. 17, 2018", w/ English claims, 15 pgs.
"Chinese Application Serial No. 201380055918.X, Response filed Aug. 23, 2019 to Office Action dated Feb. 19, 2019", w/ English Claims, 14 pgs.
"Chinese Application Serial No. 201380055918.X, Response filed Oct. 9, 2017 to Office Action dated May 19, 2017", w/ English Claims, 16 pgs.
"Chinese Application Serial No. 201380055918.X, Response filed Nov. 27, 8 to Office Action mailed", w/ English Claims, 16 pgs.
"Chinese Application Serial No. 201580058938.1, Voluntary Amendment dated Feb. 22, 2018", w/ English Claims, 21 pgs.
"European Application Serial No. 13851462.5, Communication Pursuant to Article 94(3) EPC dated Jun. 1, 2018", 9 pgs.
"European Application Serial No. 13851462.5, Extended European Search Report dated Jun. 6, 2016", 6 pgs.
"European Application Serial No. 13851462.5, Office Action dated Jun. 12, 2015", 3 pgs.
"European Application Serial No. 13851462.5, Response filed Oct. 19, 2015 to Office Action dated Jun. 12, 2015", 13 pgs.
"European Application Serial No. 13851462.5, Response filed Dec. 1, 2016 to Extended European Search Report dated Jun. 6, 2016", 20 pgs.
"European Application Serial No. 15853911.4, Extended European Search Report dated May 30, 2018", 15 pgs.
"European Application Serial No. 15853911.4, Reponse filed Nov. 12, 2018 to Extended European Search Report dated May 30, 2018", 17 pgs.
"International Application Serial No. PCT/US2015/058296, International Preliminary Report on Patentability dated May 11, 2017", 9 pgs.
"International Application Serial No. PCT/US2015/058296, International Search Report dated Jan. 21, 2016", 2 pgs.
"International Application Serial No. PCT/US2015/058296, Written Opinion dated Jan. 21, 2016", 7 pgs.
"Japanese Application Serial No. 2015-540733, Office Action dated Jul. 4, 2017", w/English Translation, 12 pgs.
"Japanese Application Serial No. 2015-540733, Office Action dated Dec. 29, 2017", With English Translation, 9 pgs.
"Japanese Application Serial No. 2015-540733, Response filed Mar. 16, 2018 to Office Action dated Dec. 29, 2017", w/ English Claims, 11 pgs.
"Japanese Application Serial No. 2015-540733, Response filed Oct. 4, 2017 to Office Action dated Jul. 4, 17", w/ English Claims, 19 pgs.
Krum, H., et al., "Catheter-based renal sympathetic denervation for resistant hypertension: a multicentre safety and proof-of-principle cohort study.", Lancet, 373(9671), (2009), 2375-1281.
"Japanese Application Serial No. 2018-153239, Response filed Oct. 1, 2019 to Notification of Reasons for Refusal dated Jul. 2, 2019", w English Claims, 10 pgs.
"U.S. Appl. No. 15/133,976, Corrected Notice of Allowability dated Nov. 20, 2019", 3 pgs.
"Chinese Application Serial No. 201580058938.1, Office Action dated Sep. 3, 2019", W English Translation, 17 pgs.
"Japanese Application Serial No. 2017-523517, Response filed Oct. 23, 2020 to Office Action dated Jun. 23, 2020", w English Claims, 14 pgs.
"European Application Serial No. 15853911.4, Response filed Oct. 27, 2020 to Communication Pursuant to Article 94(3) EPC dated Apr. 30, 2020", 14 pgs.
"Chinese Application Serial No. 201580058938.1, Response filed Nov. 24, 2020 to Office Action dated Jul. 2, 2020", w English Claims, 16 pgs.
"U.S. Appl. No. 16/156,163, Non Final Office Action dated Apr. 2, 2020", 7 pgs.
"Japanese Application Serial No. 2018-153239, Examiners Decision of Final Refusal dated Apr. 7, 2020", w English Translation, 9 pgs.
"European Application Serial No. 13851462.5, Communication Pursuant to Article 94(3) EPC dated Mar. 20, 2020", 7 pgs.
"U.S. Appl. No. 16/156,163, Response filed Jul. 1, 2020 to Non Final Office Action dated Apr. 2, 2020", 9 pgs.
"European Application Serial No. 15853911.4, Communication Pursuant to Article 94(3) EPC dated Apr. 30, 2020", 8 pgs.
"U.S. Appl. No. 16/156,163, Notice of Allowance dated Jul. 22, 2020", 5 pgs.
"Chinese Application Serial No. 201580058938.1, Office Action dated Jul. 2, 2020", w English translation, 14 pgs.
"European Application Serial No. 13851462.5, Response filed Jul. 20, 2020 to Communication Pursuant to Article 94(3) EPC dated Mar. 20, 2020", 13 pgs.
"U.S. Appl. No. 16/563,235, Notice of Allowance dated Feb. 11, 2022", 7 pgs.
"U.S. Appl. No. 16/419,587, Final Office Action dated Feb. 24, 2022", 18 pgs.
"U.S. Appl. No. 16/419,587, Response filed Mar. 9, 2022 to Final Office Action dated Feb. 24, 2022", 12 pgs.
"U.S. Appl. No. 16/690,992, Non Final Office Action dated Apr. 5, 2022", 23 pgs.
"U.S. Appl. No. 16/419,587, Notice of Allowance dated Apr. 11, 2022", 8 pgs.
"U.S. Appl. No. 16/419,587, Corrected Notice of Allowability dated Apr. 27, 2022", 5 pgs.
"Japanese Application Serial No. 2020-134047, Response filed Mar. 28, 2022 to Notification of Reasons for Refusal dated Sep. 28, 2021", wout English claims, Claims not amended in filed response, 21 pgs.
"Japanese Application Serial No. 2020-178075, Response filed Apr. 5, 2022 to Notification of Reasons for Refusal dated Jan. 5, 2022", wout English claims, Claims not amended in response filed, 5 pgs.
"Japanese Application Serial No. 2018-153239, Response filed Apr. 5, 2022 to Notification of Reasons for Refusal dated Jan. 5, 2022", W o English Claims, 8 pgs.
"U.S. Appl. No. 16/563,235, Non Final Office Action dated May 12, 2022", 16 pgs.
U.S. Appl. No. 16/563,213, filed Sep. 6, 2019, Chemical Ablation and Method of Treatment for Various Diseases.
U.S. Appl. No. 16/986,717, filed Aug. 6, 2020, Chemical Ablation and Method of Treatment for Various Diseases.
U.S. Appl. No. 16/563,235, filed Sep. 6, 2019, Chemical Ablation and Method of Treatment for Various Diseases.
U.S. Appl. No. 16/690,992, filed Nov. 21, 2019, Chemical Ablation and Method of Treatment for Various Diseases.
U.S. Appl. No. 17/329,795, filed May 25, 2021, Method of Treatment for Various Diseases.
U.S. Appl. No. 17/329,765, filed May 25, 2021, Method of Treatment for Various Diseases.
U.S. Appl. No. 17/329,823, filed May 25, 2021, Method of Treatment for Various Diseases.
U.S. Appl. No. 17/329,842, filed May 25, 2021, Method of Treatment for Various Diseases.
U.S. Appl. No. 17/010,271, filed Sep. 2, 2020, Chemical Ablation and Method of Treatment for Various Diseases.
"Japanese Application Serial No. 2017-523517, Office Action dated Jun. 23, 2020", w English translation, 14 pgs.
"U.S. Appl. No. 16/690,992, Response filed Jul. 5, 22 to Non Final Office Action dated Apr. 5, 2022", 19 pgs.
"Japanese Application Serial No. 202080044525.9, Examiners Decision of Final Refusal dated Jul. 5, 2022", w English Translation, 8 pgs.
"U.S. Appl. No. 16/690,992, Final Office Action dated Jul. 26, 2022", 12 pgs.
"U.S. Appl. No. 16/563,235, Response filed Aug. 11, 2022 to Non Final Office Action dated May 12, 2022", 11 pgs.
"U.S. Appl. No. 16/563,235, Notice of Allowance dated Aug. 26, 2022", 7 pgs.

(56) References Cited

OTHER PUBLICATIONS

"European Application Serial No. 15853911.4, Response filed Sep. 2, 2022 to Communication Pursuant to Article 94(3) EPC dated Apr. 28, 2022", 116 pgs.
"U.S. Appl. No. 16/563,213, Non Final Office Action dated Sep. 15, 2022", 9 pgs.
U.S. Appl. No. 14/438,411, filed Apr. 24, 2015, Chemical Ablation Formulations and Methods of Treatments for Various Diseases.
U.S. Appl. No. 16/419,587, filed May 22, 2019, Chemical Ablation Formulations and Methods of Treatments for Various Diseases.
U.S. Appl. No. 15/521,973 U.S. Pat. No. 10,286,191, filed Apr. 26, 2017, Chemical Ablation and Method of Treatment for Various Diseases.
U.S. Appl. No. 16/156,163, filed Oct. 10, 2018, Chemical Ablation and Method of Treatment for Various Diseases.
U.S. Appl. No. 15/133,976, filed Apr. 20, 2016, Chemical Ablation and Method of Treatment for Various Diseases.
"European Application Serial No. 13851462.5, Summons to Attend Oral Proceedings dated Jan. 28, 2022", 10 pgs.
"European Application Serial No. 13851462.5, Summons to Attend Oral Proceedings dated Feb. 28, 2022", 4 pgs.
"Chinese Application Serial No. 201910917938.2, Office Action dated May 20, 2022", w English translation, 16 pgs.
"European Application Serial No. 15853911.4, Communication Pursuant to Article 94(3) EPC dated Apr. 28, 2022", 10 ogs.
"Japanese Application Serial No. 2020-134047, Examiners Decision of Final Refusal dated Jun. 21, 2022", w English translation, 6 pgs.
"Chinese Application Serial No. 201380055918.X, Office Action dated Dec. 27, 2019", w English translation, 12 pgs.
"Japanese Application Serial No. 2017-523517, Response filed Mar. 6, 2020 to Notification of Reasons for Rejection dated Sep. 10, 2019", w English Claims, 14 pgs.
"Chinese Application Serial No. 201580058938.1, Response filed Mar. 18, 2020 to Office Action dated Sep. 3, 2019", w English Claims, 15 pgs.
"Japanese Application Serial No. 2017-523517, Notification of Reasons for Rejection dated Sep. 10, 2019", w English Translation, 13 pgs.
"Japanese Application Serial No. 2018-153239, Notification of Reasons for Refusal dated Jul. 2, 2019", W English Translation, 16 pgs.
"U.S. Appl. No. 15/133,976, Notice of Allowance dated Oct. 1, 2019", 10 pgs.
"Japanese Application Serial No. 2017-523517, Notification of Reasons for Refusal dated Jul. 6, 2021", w English Translation, 9 pgs.
"Japanese Application Serial No. 2018-153239, Notification of Reasons for Refusal dated Aug. 17, 2021", w English Translation, 17 pgs.
"Japanese Application Serial No. 2020-134047, Notification of Reasons for Refusal dated Sep. 28, 2021", w English Translation, 16 pgs.
"U.S. Appl. No. 16/563,235, Non Final Office Action dated Sep. 30, 2021", 13 pgs.
"U.S. Appl. No. 16/563,213, Notice of Allowance dated Feb. 3, 2023", 7 pgs.
"U.S. Appl. No. 16/563,213, Response filed Dec. 13, 2022 to Non Final Office Action dated Sep. 15, 2022", 7 pgs.
"U.S. Appl. No. 16/690,992, Non Final Office Action dated Feb. 6, 2023", 12 pgs.
"U.S. Appl. No. 16/690,992, Response filed Oct. 26, 2022 to Final Office Action dated Jul. 26, 2022", 12 pgs.
"Chinese Application Serial No. 201910917938.2, Office Action dated Oct. 18, 2022", w/English translation, 7 pgs.
"Chinese Application Serial No. 201910917938.2, Response filed Sep. 28, 2022 to Office Action dated May 20, 2022", w/ English Claims, 7 pgs.
"European Application Serial No. 13851462.5, invitation pursuant to Article 94(3) and Rule 710) EPC dated Oct. 11, 2022", 4 pgs.
"European Application Serial No. 13851462.5, Response filed Aug. 10, 2022 to Summons to Attend Oral Proceedings dated Feb. 28, 2022", 52 pgs.
"Japanese Application Serial No. 2018-153239, Office Action mailed Nov. 8, 2022", w/ English Translation, 45 pgs.
"Japanese Application Serial No. 2020-178075, Preliminary Examination Report dated Jan. 24, 2023", w/ English Translation, 2 pgs.
"Japanese Application Serial No. 2020-178075, Response field Dec. 21, 2022 to Office Action dated Nov. 22, 2022", w/English Translation, 11 pgs.
"Japanese Application Serial No. 202080044525.9, Response filed Nov. 7, 2022 to Examiners Decision of Final Refusal dated Jul. 5, 2022", w/ English Claims, 13 pgs.

* cited by examiner

CHEMICAL ABLATION FORMULATIONS AND METHODS OF TREATMENTS FOR VARIOUS DISEASES

CROSS-REFERENCE TO RELATED APPLICATIONS

This application is a continuation of U.S. application Ser. No. 16/419,587, filed May 22, 2019 continuation of U.S. application Ser. No. 14/438,411, filed Apr. 24, 2015, which claims the benefit of U.S. National Stage Filing under 35 U.S.C. 371 from International Application No. PCT/US2013/067382, filed Oct. 30, 2013, which claims benefit of U.S. Provisional Application No. 61/796,118, filed Nov. 2, 2012, Application Ser. No. 61/797,647, filed Dec. 12, 2012, Application Ser. No. 61/848,483, filed Jan. 4, 2013, and Application Ser. No. 61/849,928, filed Feb. 5, 2013, which are hereby incorporated herein by reference in their entirety.

TECHNICAL FIELD

Embodiments of the present invention relate to chemical ablation formulations, combination of thermal and chemical ablations, and methods of treatments for diseases, such as hypertension, diabetes, obesity, heart failure, end-stage renal disease, digestive diseases, urological diseases, cancers, tumors, pains, asthma, pulmonary arterial hypertension, and chronic obstructive pulmonary disease (COPD). The formulations include gases, vapors, liquids, solutions, emulsions, and suspensions of one or more ingredients. The methods involve chemical ablation by delivering the formulations or/and thermal energy to the target of diseased tissues of human body.

BACKGROUND

Hypertension, or high blood pressure, is a major global public health concern. An estimated 30-40% of the adult population in the world suffers from this condition. Furthermore, its prevalence is expected to increase, especially in developing countries. Diagnosis and treatment of hypertension remain suboptimal and most of patients cannot attain adequate blood-pressure control to guideline target values. Thus, the development of new approaches for the management of hypertension is needed, especially those patients with so-called resistant hypertension. These patients fail to control blood pressure to the target despite multiple drug therapies at the highest tolerated dose.

Hypertension is caused by hyperactive renal sympathetic nerves. Renal sympathetic efferent and afferent nerves run generally longitudinally along the outside of arteries leading from the aorta to the kidneys. These nerves are critically important in the initiation and maintenance of systemic hypertension. It has been shown that by severing these nerves, blood pressure can be reduced. Exemplary experiments have shown that denervation of the renal sympathetic nerves in rats with hyperinsulinimia-induced hypertension would reduce the blood pressure to normotensive levels as compared to controls [Huang W-C, et al. Hypertension 1998; 32:249-254].

While renal denervation had been performed with surgical methods in the past, more recently a catheter-based therapy to heat and destroy the nerves from within the renal artery using radio-frequency ablation has been studied. A human trial of the RF-ablation catheter method has also been performed, with reported reduction in blood pressure in patients enrolled in the catheter treatment arm of the study [Krum H, et al. Lancet 2009; 373(9671):1228-1230].

Benign prostatic hyperplasia is a non-cancerous enlargement of the prostate gland, affecting more than 50% percent of men over the age of 60. The prostate early in life is the size and shape of a walnut and weight about 20 grams. Prostate enlargement appears to be a normal process. With age, the prostate gradually increases in size to twice or more its normal size. As the prostate grows, it presses against and narrows the urethra, causing a urinary obstruction that makes it difficult to urinate.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S. Chronic bronchitis is inflammation of the bronchial airways. The bronchial airways connect the trachea with the lungs. When inflamed, the bronchial tubes secrete mucus, causing a chronic cough. Emphysema is an overinflation of the alveoli, or air sacs in the lungs. This condition so causes shortness of breath.

Asthma is a chronic respiratory disease characterized by inflammation of the airways, excess mucus production and airway hyper responsiveness, and a condition in which airways narrow excessively or too easily respond to a stimulus. Asthma episodes or attacks cause narrowing of the airways, which make breathing difficult. Asthma attacks can have a significant impact on a patient's life, limiting participation in many activities. In severe cases, asthma attacks can be life threatening. Presently, there is no known cure for asthma.

Pulmonary arterial hypertension (PAH) is defined as a group of diseases characterized by elevations of mean pulmonary artery pressure and a progressive increase in pulmonary vascular resistance resulting in right heart failure and premature death. Recent targeted therapies have advanced the treatment. However, there is no cure for PAH and it remains a life-threatening disorder. The preliminary safety and efficacy of pulmonary artery radio-frequency denervation for PAH patients have been reported.

Chronic sinusitis is an inflammation of the membrane lining of one or more paranasal sinuses. Chronic sinusitis lasts longer than three weeks and often continues for months. In cases of chronic sinusitis, there is usually tissue damage. According to the Center for Disease Control (CDC), thirty seven million cases of chronic sinusitis are reported annually.

Radio frequency (RF) ablation has been used in treatments of hypertension, asthma and chronic obstructive pulmonary disease (COPD). While the use of catheter-based radiofrequency (RF) denervation appears to have a therapeutic effect, it is unknown what long-term implications will arise from the permanent damage caused to the vessel wall and nerves by the RF procedure. Radiofrequency energy denervates the vessel by creating heat in the vessel wall. The RF probe contacts the inner lining of the artery and the RF energy is transmitted through the tissue. It lacks fine control. It may cause damage to the endothelium and smooth muscles, resulting in vessel injury and occlusion. The SYMPLICITY HTN-2 trial shows that there are three groups of patients. About 10% are non-responders; 39% are excellent responders, with blood pressure going below 140 mmHg; and in between there are 50% of patients with some response, with at least 10 mmHg drops, but at the moment we do not know what the clinical relevance of this drop is. The safety and efficacy need to improve for most of patients with hypertension.

A variety of ablative techniques have been developed to complement the traditional surgical and oncologic approaches used in treating tumors. These techniques including transarterial chemoembolization, percutaneous ablation with chemicals such as alcohol or acetic acid, or percutaneous treatment with radiofrequency ablation or cryotherapy. The regional and local ablative techniques used in the treatment of hepatic tumors have been studied extensively and they have been used in treating a variety of other tumors recently. Systemic chemotherapy and external beam radiation therapy have limitations due to poor tumor response and toxicity. New ablation methods are needed to improve safety and efficacy of treatments.

SUMMARY

Disclosed are methods for the treatment of diseases, such as hypertension, diabetes, obesity, heart failure, end-stage renal disease, digestive disease, urological disease, cancers, tumors, pains, asthma, pulmonary arterial hypertension, and chronic obstructive pulmonary disease (COPD). In some embodiments, the methods involve delivering an effective amount of a formulation to target diseased tissues. The formulation can comprise gases, vapors, liquids, solutions, emulsions, or suspensions of one or more ingredients. The methods involve delivering the formulations at various temperatures to tissues of human body. The temperature may enhance safety and efficacy of the formulations for the treatments. Suitable temperature can be in the range of −40 to 140° C., preferable in the range of −30 to 100° C., most preferable in the range of −30 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM. The formulation is one of binary, ternary, four component, or more than four component formulations. The delivery system can be a percutaneous or less invasive delivery method. In some embodiments, the formulation comprises one or more ingredients that enhance absorption and penetration into the nerves of body lumens.

In some embodiments, the methods involve delivering of an effective amount of energy and formulations to target nerves. For example, the energy can be selected from the group consisting of radiofrequency, cryoablation, microwave, laser, ultrasound, and high-intensity focused ultrasound energies. As above, the formulations can include gases, vapors, liquids, solutions, emulsions, and suspensions of one or more ingredients. The methods can involve the combination of thermal and chemical ablation, their formulations, and methods for treatments of hypertension, diabetes, obesity, heart failure, end-stage renal disease, digestive disease, urological disease, asthma, pulmonary arterial hypertension and chronic obstructive pulmonary disease (COPD) by thermal and chemical ablations to nerves of human body at various temperatures. The thermal energy may enhance safety and efficacy of the chemical ablation for the treatments. The chemical ablation may improve safety and efficacy of thermal ablation for the treatments by lowing ablation temperature and time. The temperature can be in the range of −40 to 140° C., preferable in the range of −30 to 100° C., most preferable in the range of −30 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM. The formulation can be one of binary, ternary, four component, or more than four component formulations. The delivery system can be a percutaneous less invasive delivery catheter. The formulation delivery catheter can be a needle based catheter. The formulation delivery catheter can also be a balloon based catheter. The balloon based catheter can have single or double balloons. The formulation delivery catheters can be an infusion catheter. The energy delivery catheter can be selected from the group consisting of radiofrequency, cryoablation, microwave, laser, ultrasound, and high-intensity focused ultrasound delivery catheters. In some embodiments, the disclosed methods provide a combination of thermal energy and formulation comprising one or more ingredients that enhance absorption and penetration into the nerves of body lumens.

In some embodiments, the disclosed methods improve safety and efficacy of radiofrequency ablation by increasing ablation size, while minimizing the risks for complications that can arise during the heating. Examples of such complications include thrombus formation, steam pops, bubbling, charring on the lesion, restenosis, fibrosis in the media and the adventitia, and others related to catheter manipulation (i.e., perforations). Spot thermal ablation (RF ablation) is not uniform and it does not reach to the nerves in adventitia. Partially spot RF ablation leads to low efficacy (low blood pressure drops). Complications can be minimized by reducing the electrode size (leading to passive cooling via the blood flow) and cooling the electrode through active fluids, cooling either internally (closed-loop) or externally (open-loop). Cooling the electrodes increases energy delivery into the nerve tissue. In one embodiment of externally cooling (open-loop), the chemical formulation can replace the active cooling fluids. The disclosed formulation can be used not only for cooling electrodes, but also used for chemical ablation. Therefore, the chemical ablation formulation can be delivered during, before, and after the thermal ablations. Thermal ablations include radiofrequency, cryoablation, microwave, laser, ultrasound, and high-intensity focused ultrasound ablations.

In some embodiments, the ingredient of the formulation is chosen from water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, urea, lipiodol, surfactant, derivatives and combinations thereof.

In some embodiments, the ingredient of the formulation comprises one or more gases. Suitable gases include oxygen, nitrogen, helium, argon, air, carbon dioxide, nitric oxide, vapors of organic and inorganic compounds, water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, derivatives and combinations thereof.

In some embodiments, the ingredient of the formulation comprises one or more surfactants. Examples of surfactants include PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methyl-glucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methyl-glucamide, n-octyl-β-D-glucopyranoside, octyl-β-D-thio-glucopyranoside, benzalkonium chloride, benzethonium chloride, docecyl trimethyl ammonium bromide, sodium ricinoleate, dioctyl sodium sulfosuccinate, sodium lauryl sulfate, sodium docecylsulfates, dialkyl methylbenzyl ammonium chloride, and dialkylesters of sodium sulfonsuccinic acid, organic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, Pluronic, Pluronic 85, and derivatives and combinations thereof.

In some embodiments, the formulation comprises at least one oil, fatty acid, or lipid. Examples include soybean oil, vegetable oil, flower oil, animal oil, marine oil, butterfat, coconut oil, palm oil, olive oil, peanut oil, fish oil, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or tria-cylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, and derivatives thereof.

In some embodiments, the formulation includes one or more therapeutic agents or drugs for nerve denervation. Examples of therapeutic agents include sodium channel blockers, tetrodotoxin, saxitoxin, decarbamoyl saxitoxin, vanilloids, neosaxitoxin, lidocaine, conotoxins, cardiac glycosides, digoxin, glutamate, staurosporine, amlodipine, verapamil, cymarin, digitoxin, proscillaridin, quabain, veratridine, domoic acid, oleandrin, carbamazepine, aflatoxin, guanethidine, and guanethidine sulfate. In another embodiment, the formulation includes one of the contrast agents for imaging nerve denervation. The contrast agent includes iodine, ethyl iodide, sodium iodide, lipiodol, nonoxynol iodine, iobitridol, iohexol, iomeprol, iopamidol, iopentol, iopromide, ioversol, ioxilan, iotrolan, iodixanol, ioxaglate, and their derivatives.

In some embodiments, the formulation includes an azeotrope. An azeotrope is a mixture of two or more ingredients in such a way that its components cannot be altered by simple distillation. This happens because the vapor it produces has proportionate constituents as the original mixture when an azeotrope is boiled. Example azeotropes of the formulations include ethanol/water, ethanol/water/contrast agent, ethanol/water/surfactant, ethanol/water/contrast agent/surfactant, propanol/water, iso-propanol/water, butanol/water, acetic acid/water, acetic acid/water/ethanol, acetic acid/water/contrast agent, acetic acid/water/contrast agent/surfactant, acetic acid/water/ethanol/contrast agent, acetic acid/water/ethanol/contrast agent/surfactant, lactic acid/water, lactic acid/water/ethanol, lactic acid/water/contrast agent, lactic acid/water/contrast agent/surfactant, lactic acid/water/ethanol/contrast agent, lactic acid/water/ethanol/contrast agent/surfactant, ethyl lactate/water, ethyl lactate/ethanol, lactic acid/ethanol/water, ethyl lactate/water/ethanol, ethyl acetate/ethanol, ethyl nitrate/ethanol, isopropyl acetate/ethanol, and their combinations.

In some embodiments, the formulation is in state of gases or vapors of one or more ingredients. Example vapor or gas formulation includes oxygen, nitrogen, helium, argon, air, carbon dioxide, nitric oxide, water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate and their mixtures. The vapor formulation may include a surfactant. The vapor formulation may include a therapeutic agent. The vapor formulation can include a contrast agent, such as lipiodol, iodine. The vapor can include an azeotrope. The vapor can be one of binary, ternary, four component, or more than four component formulations. The elevated temperature of the vapor formulation can be in the range of 0-140° C., preferable of 15-100° C., most preferable of 20-85° C. The pressure of the vapor infused is higher than body lumen pressure (1 ATM). The pressure range of the vapor infused to the target tissue is from 1 to 12 ATM, or 1 to 8 ATM or 1 to 5 ATM, preferred 1 to 3 ATM.

In some embodiments, the formulation is in state of liquid of one or more ingredients. Example liquid formulations include water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, lipiodol, methyl acetate, ethyl acetate, ethyl nitrate, isopropyl acetate, ethyl lactate, urea, surfactant, and others. The liquid formulation may include a therapeutic agent. The liquid formulation may include a contrast agent. The liquid formulation may include an azeotrope. The liquid formulation can be one of binary, ternary, four component, or more than four component formulations. The desired temperature of the liquid formulation can be in the range of −40 to 140° C., preferable of −30 to 100° C., most preferable of −20 to 80° C. The pressure of the liquid infused is higher than body lumen pressure (1 ATM). The pressure range of the liquid infused to the target tissue is from 1 to 12 ATM, or 1 to 8 ATM or 1 to 5 ATM, preferred 1 to 3 ATM. The liquid formulation can include a solution. The liquid formulation can include a suspension. The liquid formulation includes an emulsion.

In some embodiments, the method for treating a diseases involves inserting a delivery catheter percutaneously into the diseased tissues of a human body, infusing the formulation through the catheter to the tissues of the body, wherein the amount of the formulation and/or heat or cool delivered is effective to injury or damage the tissues to have a therapeutic benefit (e.g., neuromodulation, lowering blood pressure, treating shortness of breath), and withdrawing the delivery catheter from the body. Heating or cooling can be used to enhance the effect by accelerating reaction rates of the formulation and the tissues. Example diseases include hypertension, diabetes, obesity, heart failure, end-stage renal disease, digestive disease, urological disease, cancers, tumors, pains, asthma, pulmonary arterial hypertension, and chronic obstructive pulmonary disease (COPD). Example body tissues includes renal arteries, vascular lumen, nonvascular lumen, airway, sinus, esophagus, respiratory lumens, digestive lumens, cancers, tumors, pains, and urological lumens. Example formulations include gases, vapors, liquids, solutions, emulsion, and suspensions of one or more ingredients. If the formulation is a vapor of one or more ingredients, the heat can be generated by condensation of the vapors into liquids in the tissue. If the formulation is a liquid or solutions, the cool or heat can be generated by the temperature of the formulation (i.e., above or below body temperature). The temperature of the liquid formulation can be in the range of −40 to 140° C., preferable of −30 to 100° C., most preferable of −20 to 80° C. The temperature of the formulations can be at room temperature in one embodiment. The temperature of the formulations is in the range of −40 to −20° C. in some embodiments. The temperature of the formulations is in the range of 15 to 80° C. in some embodiments. The temperature of the formulations is at body temperature in some embodiments. The temperature of the formulations is in the range of 50 to 80° C. in some embodiments. The temperature of the treated tissue is lower than the desired temperature of the formulation and higher than that of body temperature in some embodiments. The temperature of the treated tissue can be in the range of −40 to 100° C., preferable of −30 to 80° C., most preferable of −20 to 80° C. The temperature of the treated tissue is in the range of −40 to −20° C. in some embodiments. The temperature of the treated tissue is in the range of 15 to 80° C. in some embodiments. The temperature of the treated tissue is at body temperature in some embodiments. The temperature of the treated tissue is in the range of 50 to 80° C. in some embodiments. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM. The delivery catheter is a needle or needle based catheter under imaged guide. For example, the imaged guide can be ultrasound, X-ray, CT scan, scopes, or a combination thereof. The delivery catheter can be a balloon based catheter. For example, the balloon based catheter can have single or double balloons. The delivery catheter can be an infusion catheter. In some embodiments, the catheter is a combination of balloon catheter and infusion catheter.

In some embodiments, the method for treating diseases includes inserting an irrigated thermal ablation catheter percutaneously into the body lumen adjacent to nerves, infusing the formulation to the tissue of the body lumen adjacent to the nerves; thermally ablating the tissue of the body lumen adjacent to the nerves; infusing the formulation during, before, and/or after the thermal ablation, wherein the amount of formulation and/or energy delivered is effective to injury or damage the nerves to have a benefit, such as lower blood pressure and shortness of breath; and withdrawing the irrigated thermal ablation catheters from the body lumen. The irrigated thermal ablation catheters can be selected from the group consisting of radiofrequency, cryoablation, microwave, laser, ultrasound, and high-intensity focused ultrasound irrigated ablation catheters. The energy can enhance the effect by accelerating reaction rate of the formulation and the nerves. The diseases can be selected from the group consisting of hypertension, diabetes, obesity, heart failure, end-stage renal disease, digestive disease, urological disease, asthma, pulmonary arterial hypertension, and chronic obstructive pulmonary disease (COPD). The body lumen can comprise renal arteries, vascular lumen, nonvascular lumen, airway, sinus, esophagus, respiratory lumens, digestive lumens, and/or urological lumens. The formulations can be selected from the group consisting of gases, vapors, liquids, solutions, emulsion, and suspensions of one or more ingredients. If the formulation comprises vapors of one or more ingredients, the heat can be generated by condensation of the vapors into liquids in the tissue. If the formulation is liquids or solutions, the cool or heat can be generated by the temperature of the formulation above or below body temperature. The temperature of the liquid formulation can be in the range of −40 to 140° C., preferable in the range of −30 to 100° C., most preferable in the range of −20 to 80° C. The temperature of the formulations is at room temperature in some embodiments. The temperature of the formulations is in the range of −40 to −20° C. in some embodiments. The temperature of the formulations is in the range of 15 to 80° C. in some embodiments. The temperature of the formulations is at body temperature in some embodiments. The temperature of the formulations is in the range of 50 to 80° C. in some embodiments. The temperature of the treated tissue adjacent to the nerves is lower than the desired temperature of the formulation and higher than that of body temperature in some embodiments. The temperature of the treated tissue adjacent to the nerves can be in the range of −40 to 100° C., preferable in the range of −30 to 80° C., most preferable in the range of −20 to 80° C. The temperature of the treated tissue adjacent to the nerves is in the range of −40 to −20° C. in some embodiments. The temperature of the treated tissue adjacent to the nerves is in the range of 15 to 80° C. in some embodiments. The temperature of the treated tissue adjacent to the nerves is at body temperature in some embodiments. The temperature of the treated tissue adjacent to the nerves is in the range of 50 to 80° C. in some embodiments. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the combination of non-irrigated thermal ablation catheter and the formulation delivery catheter can be used alternatively or simultaneously for treatment of a disease. The method for treating diseases can comprise inserting a non-irrigated thermal ablation catheter or/and a formulation delivery catheter percutaneous into the body lumen adjacent to nerves; infusing the formulation to the tissue of the body lumen adjacent to the nerves; thermally ablating the tissue of the body lumen adjacent to the nerves; infusing the formulation during, before, and/or after the thermal ablation, wherein amount of the formulation and/or energy delivered is effective to injury or damage the nerves to have a benefit, such as lower blood pressure and shortness of breath; and withdrawing the non-irrigated thermal ablation catheter or/and the formulation delivery catheter from the body lumen. The non-irrigated thermal ablation catheters can be selected from the group consisting of radiofrequency, cryoablation, microwave, laser, ultrasound, and high-intensity focused ultrasound non-irrigated ablation catheters. The formulation delivery catheter can be a needle based catheter. The formulation delivery catheter can also a balloon based catheter. The balloon based catheters can have single or double balloons. The formulation delivery catheters can be an infusion catheter. The energy can enhance the effect by accelerating reaction rate of the formulation and the nerves. The diseases can be selected from the group consisting of hypertension, diabetes, obesity, heart failure, end-stage renal disease, digestive disease, urological disease, asthma, pulmonary arterial hypertension, and chronic obstructive pulmonary disease (COPD). The body lumen can be selected from the group consisting of renal arteries, vascular lumen, nonvascular lumen, airway, sinus, esophagus, respiratory lumens, digestive lumens, and urological lumens. The formulations be selected from the group consisting of gases, vapors, liquids, solutions, emulsion, and suspensions of one or more ingredients. If the formulation is vapors of one or more ingredients, the heat can be generated by condensation of the vapors into liquids in the tissue. If the formulation is liquids or solutions, the cool or heat can be generated by the temperature of the formulation above or below body temperature. The temperature of the liquid formulation can be in the range of −40 to 140° C., preferable in the range of −30 to 100° C., most preferable in the range of −20 to 80° C. The temperature of the formulations is at room temperature in some embodiments. The temperature of the formulations is in the range of −40 to −20° C. in some embodiments. The temperature of the formulations is in the range of 15 to 80° C. in some embodiments. The temperature of the formulations is at body temperature in some embodiments. The temperature of the formulations is in the range of 50 to 80° C. in some embodiments. The temperature of the treated tissue adjacent to the nerves is lower than the desired temperature of the formulation and higher than that of body temperature in some embodiments. The temperature of the treated tissue adjacent to the nerves can be in the range of −40 to 100° C., preferable in the range of −30 to 80° C., most preferable in the range of −20 to 80° C. The temperature of the treated tissue adjacent to the nerves is in the range of −40 to −20° C. in some embodiments. The temperature of the treated tissue adjacent to the nerves is in the range of 15 to 80° C. in some embodiments. The temperature of the treated tissue adjacent to the nerves is at body temperature in some embodiments. The temperature of the treated tissue adjacent to the nerves is in the range of 50 to 80° C. in some embodiments. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

It is understood that both the foregoing general description and the following detailed description are exemplary and explanatory only and are not restrictive of the present invention as claimed.

DETAILED DESCRIPTION

Figure 1:
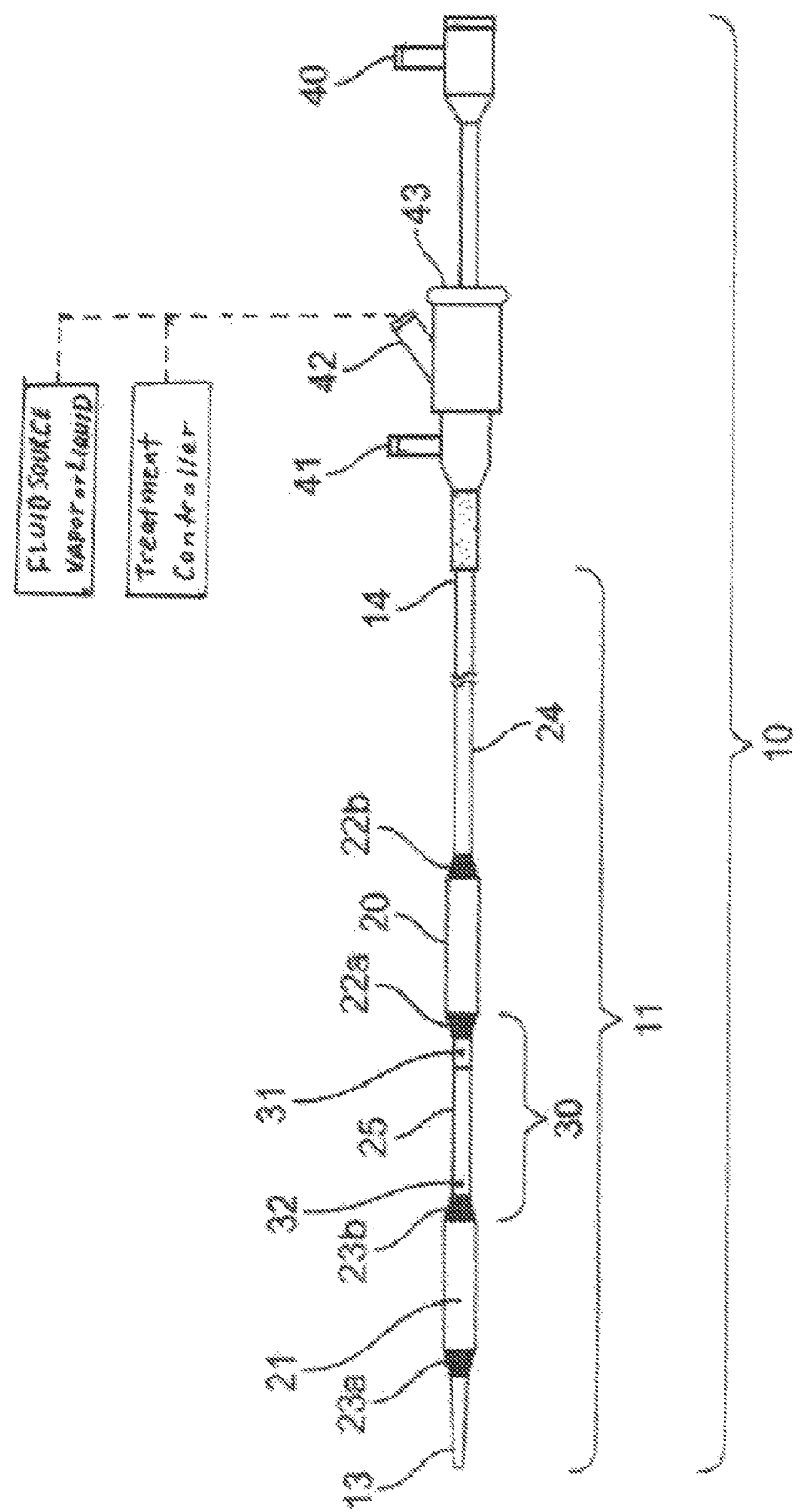
FIG. 1 is a perspective view of an exemplary embodiment of a double balloon delivery catheter embodiment.

Disclosed are embodiments directed to the treatment of a disease by delivering an effective amount of a formulation to target tissues, such as diseased tissue. The term "diseased tissue" includes any tissue that contributes to a disease. For example, the disease can be one of hypertension, diabetes, obesity, heart failure, end-stage renal disease, digestive disease, urological disease, cancer, tumor, pains, asthma, pulmonary arterial hypertension, and chronic obstructive pulmonary disease (COPD). Example cancers include adrenal, bladder, cervical, colon, esophageal, gallbladder, kidney, liver, lung, ovarian, pancreatic, prostatic, rectal, stomach, and uterine cancers. The formulation comprise one or more gases, vapors, liquids, solutions, emulsions, and suspensions of one or more ingredients. The methods can involve delivering the formulations at desired temperature to tissues of human body. Example tissues include renal arteries, vascular lumen, nonvascular lumen, airway, sinus, esophagus, respiratory lumens, digestive lumens, cancers, tumors, and urological lumens. The temperature may enhance safety and efficacy of the formulations for the treatments. The temperature can be in the range of −40 to 140° C., preferable of −30 to 100° C., most preferable of −20 to 80° C. The temperature of the treated tissue can be different from the temperature of the formulation. The temperature of the treated tissue can be in the range of −40 to 100° C., preferable of −30 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM. The amount of the formulation and energy delivered is preferably effective to injure or damage or eliminate diseased tissues to have a therapeutic benefit, such as lowering blood pressure, shrinking tumors, relieving pains, relieving symptoms of asthma, pulmonary arterial hypertension, and treating COPD. Energy or heat can in some embodiments enhance the effect by accelerating reaction rates of the formulation and the tissues.

Disclosed are embodiments directed to the treatment of a disease by delivering of an effective amount of energy or/and formulations to target nerve tissue. For example, the disease can be selected from the group consisting of hypertension, diabetes, obesity, heart failure, end-stage renal disease, digestive disease, urological disease, asthma, pulmonary arterial hypertension, and chronic obstructive pulmonary disease (COPD). The energy can be radiofrequency, cryoablation, microwave, laser, ultrasound, and/or high-intensity focused ultrasound energies. The formulations can be gases, vapors, liquids, solutions, emulsions, and/or suspensions of one or more ingredients. The methods can involve the combination of thermal and chemical ablation, their formulations, and methods for treatments of hypertension, diabetes, obesity, heart failure, end-stage renal disease, digestive disease, urological disease, asthma, pulmonary arterial hypertension and chronic obstructive pulmonary disease (COPD) by thermal and chemical ablations to nerves of human body at various temperatures. The thermal energy may enhance safety and efficacy of the chemical ablation for the treatments. The chemical ablation may improve safety and efficacy of thermal ablation for the treatments by lowing ablation temperature and/or time. The temperature can be in the range of −40 to 140° C., preferable in the range of −30 to 100° C., most preferable in the range of −30 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM. The formulation can be one of binary, ternary, four component, or more than four component formulations. The delivery system can be a percutaneous less invasive delivery catheter.

The disclosed methods can provide a combination of thermal energy and formulation comprising one or more ingredients that enhance absorption and penetration into the nerves of body lumens.

In some embodiments, safety and efficacy of the radiofrequency ablation is improves by increasing ablation size, while minimizing risks for complications that can arise during the heating. Examples of such complications include thrombus formation, steam pops, bubbling, charring on the lesion, restenosis, fibrosis in the media and the adventitia, and others related to catheter manipulation (i.e., perforations). Spot thermal ablation (RF ablation) is not uniform and it does not reach to the nerves in adventitia. Partially spot RF ablation leads to low efficacy (low blood pressure drops). The methods include the electrode size (passive cooling via the blood flow) and cooling the electrode through active fluids cooling either internally (closed-loop) or externally (open-loop). Cooling electrodes increases energy delivery into the nerve tissue. In one embodiment of externally cooling (open-loop), the chemical formulation can replace the active cooling fluids. The disclosed formulations can be used not only for cooling electrodes, but also used for chemical ablation. The formulations can in some embodiments diffuse and permeate into the nerve tissue uniformly, and they can ablate the nerves in adventitia uniformly in the body lumen. Therefore, the chemical ablation formulation can be delivered during, before, and/or after the thermal ablations. Examples of thermal ablations include radiofrequency, cryoablation, microwave, laser, ultrasound, and high-intensity focused ultrasound. Therefore, the methods can improve safety and efficacy of the treatments.

The formulation can be one of binary, ternary, four component, or more than four component formulations. The delivery system can be a percutaneous, less invasive delivery method. Also provided is a formulation comprising one or more ingredients that enhance absorption and penetration into tissues of the body lumens.

In some embodiments, the ingredient of the formulation is chosen from water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, urea, lipiodol, surfactant, derivatives and combinations thereof.

In some embodiments, the ingredient of the formulation is a gas. Example gases include oxygen, nitrogen, helium, argon, air, carbon dioxide, nitric oxide, vapors of organic and inorganic compounds, water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate, and their mixtures.

In some embodiments, the ingredient in the formulation is a surfactant. Example surfactants include PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG lauryl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside, benzalkonium chloride, benzethonium chloride, docecyl trimethyl ammonium bromide, sodium ricinoleate, dioctyl sodium sulfosuccinate, sodium lauryl sulfate, sodium docecylsulfates, dialkyl methylbenzyl ammonium chloride, and dialkylesters of sodium sulfonsuccinic acid, organic acid, salts of any organic acid and organic amine, polyglycidol, glycerol, multiglycerols, galactitol, di(ethylene glycol), tri(ethylene glycol), tetra (ethylene glycol), penta(ethylene glycol), poly(ethylene glycol) oligomers, di(propylene glycol), tri(propylene glycol), tetra(propylene glycol, and penta(propylene glycol), poly (propylene glycol) oligomers, a block copolymer of polyethylene glycol and polypropylene glycol, Pluronic, Pluronic 85, and derivatives and combinations thereof. The content of the surfactant in the formulation can be in the range of 0.1 to 80% by weight, preferably 0.5 to 50% by weight, most preferably 1 to 15% by weight.

In some embodiments, at least one oil, fatty acid, and/or a lipid is in the formulation. For example, the formulation can comprise soybean oil, vegetable oil, flower oil, animal oil, marine oil, butterfat, coconut oil, palm oil, olive oil, peanut oil, fish oil, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, and derivatives thereof.

In some embodiments, the formulation includes one or more therapeutic agents or drugs for nerve denervation. The therapeutic agent can be one of sodium channel blockers, tetrodotoxin, saxitoxin, decarbamoyl saxitoxin, vanilloids, neosaxitoxin, lidocaine, conotoxins, cardiac glycosides, digoxin, glutamate, staurosporine, amlodipine, verapamil, cymarin, digitoxin, proscillaridin, quabain, veratridine, domoic acid, oleandrin, carbamazepine, aflatoxin, guanethidine, and guanethidine sulfate. In another embodiment, the formulation includes one of the contrast agents for imaging nerve denervation. The contrast agent can includes iodine, ethyl iodide, sodium iodide, lipiodol, nonoxynol iodine, iobitridol, iohexol, iomeprol, iopamidol, iopentol, iopromide, ioversol, ioxilan, iotrolan, iodixanol, ioxaglate, and their derivatives. The content of the contrast agent in the formulation can be in the range of 2 to 25% by weight, preferable 5 to 15% by weight.

In some embodiments, the formulation includes an azeotrope. An azeotrope is a mixture of two or more ingredients in such a way that its components can not altered by simple distillation. This happens because the vapor it produces has proportionate constituents as the original mixture when an azeotrope is boiled. The azeotropes or the formulations can include ethanol/water, ethanol/water/contrast agent, ethanol/water/surfactant, ethanol/water/contrast agent/surfactant, propanol/water, iso-propanol/water, butanol/water, acetic acid/water, acetic acid/water/ethanol, acetic acid/water/contrast agent, acetic acid/water/contrast agent/surfactant, acetic acid/water/ethanol/contrast agent, acetic acid/water/ethanol/contrast agent/surfactant, lactic acid/water, lactic acid/water/ethanol, lactic acid/water/contrast agent, lactic acid/water/contrast agent/surfactant, lactic acid/water/ethanol/contrast agent, lactic acid/water/ethanol/contrast agent/surfactant, ethyl lactate/water, ethyl lactate/ethanol, lactic acid/ethanol/water, ethyl lactate/water/ethanol, ethyl acetate/ethanol, ethyl nitrate/ethanol, and isopropyl acetate/ethanol.

In some embodiments, the formulation is in state of gases or vapors of one or more ingredients. The gas or vapor formulation can comprise oxygen, nitrogen, helium, argon, air, carbon dioxide, nitric oxide, and vapors of organic and inorganic compounds. The vapors of the organic and inorganic compounds can include water, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, methyl acetate, ethyl acetate, ethyl nitrate, isopropyl acetate, ethyl lactate and their mixtures.

The vapor formulation may include a surfactant. The vapor formulation may include a therapeutic agent. The vapor formulation may include a contrast agent, such as lipiodol and iodine. The vapor may include an azeotrope. The vapor can be one of binary, ternary, four component, or more than four component formulations. The desired temperature of the vapor formulation can be in the range of 0 to 140° C., preferable of 15 to 100° C., most preferable of 30 to 80° C. The pressure of the vapor infused is higher than body lumen pressure (1 ATM). The pressure range of the vapor infused to the target tissue is from 1 to 12 ATM, or 1 to 8 ATM or 1 to 5 ATM, preferred 1 to 3 ATM.

In some embodiments, the formulation is in state of liquid of one or more ingredients. The liquid formulation can include water, saline, hypertonic saline, phenol, methanol, ethanol, absolute alcohol, isopropanol, propanol, butanol, isobutanol, ethylene glycol, glycerol, acetic acid, lactic acid, propyl iodide, isopropyl iodide, ethyl iodide, lipiodol, methyl acetate, ethyl acetate, ethyl nitrate, isopropyl acetate, ethyl lactate, urea, surfactant, and others. The liquid formulation may include a therapeutic agent. The liquid formulation may include a contrast agent. The liquid formulation may include an azeotrope. The liquid formulation can be one of binary, ternary, four component, or more than four component formulations. The liquid formulation may be a solution. The liquid formulation may be an emulsion. The liquid formulation may be a suspension. The temperature of the liquid formulation can be in the range of −40 to 140° C., preferably in the range of −30 to 100° C., most preferably in the range of −30 to 80° C. The temperature of the formulations is at room temperature in some embodiments. The temperature of the formulations is in the range of −40 to −20° C. in some embodiments. The temperature of the formulations is in the range of 15 to 80° C. in some embodiments. The temperature of the formulations is at body temperature in some embodiments. The temperature of the formulations is in the range of 50 to 80° C. in some embodiments. The pressure of the liquid infused is higher than body lumen pressure (1 ATM). The pressure range of the liquid infused to the target tissue is from 1 to 12 ATM, or 1 to 8 ATM or 1 to 5 ATM, preferred 1 to 3 ATM.

In some embodiments, the method for treating a diseases includes inserting a delivery catheter percutaneously into the body; infusing the formulation through the catheter to the diseased tissue of the body, wherein amount of the formulation and/or heat or cool delivered is effective to injury or damage the tissues to have a therapeutic benefit (e.g., lower blood pressure and shortness of breath), and withdrawing the delivery catheter from the body. Heat or cool can enhance the effect by accelerating reaction rate of the formulation and the tissues. Example diseases that can be treated include hypertension, diabetes, obesity, heart failure, end-stage renal disease, digestive disease, urological disease, cancers, tumors, pains (chronic and/or acute), asthma, pulmonary arterial hypertension, and chronic obstructive pulmonary disease (COPD). Cancers include adrenal, bladder, cervical, colon, esophageal, gallbladder, kidney, liver, lung, ovarian, pancreatic, prostatic, rectal, stomach, and uterine cancers. Body tissues include renal arteries, vascular lumen, nonvascular lumen, airway, sinus, esophagus, respiratory lumens, digestive lumens, cancers, tumors, and urological lumens. The formulation can be a gas, vapor, liquid, solution, emulsion, or suspension comprising one or more ingredients. If the formulation is a vapor of one or more ingredients, the heat can be generated by condensation of the vapors into liquids in the tissue. If the formulation is a liquid or solution, the cool or heat can be generated by the temperature of the formulation, i.e., below or above body temperature. The temperature of the liquid formulation can be in the range of −40 to 140° C., preferably in the range of −30 to 100° C., most preferably in the range of −30 to 80° C. The temperature of the treated tissue can be different from the temperature of the formulation and lower or higher than that of body temperature in some embodiments. The temperature of the treated tissue can be in the range of 15-100° C., preferably in the range of 20-90° C., most preferably in the range of 36-80° C. The temperature of the treated tissue can be in the range of −40 to −20° C. in some embodiments. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM. The delivery catheter can be a needle or a needle based catheter under imaged guide. The imaged guide can be one of ultrasound, X-ray, CT-scan, and scopes. The delivery catheter can also be a balloon based catheter. Balloon based catheters can have at least one or two balloons. The delivery catheter can be an infusion catheter. The catheter can be a combination of balloon catheter and an infusion catheter.

In some embodiments, the method for treating disease includes inserting a delivery catheter percutaneously into the body lumen adjacent to nerves; delivering the energy or/and the formulation above described at a desired temperature to the tissue of the body lumen adjacent to the nerves, wherein the amount of formulation and/or energy delivered is effective to injury or damage the nerves to have a benefit, such as lower blood pressure; and withdrawing the delivery catheters from the body lumen. Example diseases that can be treated include hypertension, diabetes, obesity, heart failure, end-stage renal disease, digestive disease, urological disease, cancers, tumors, pains (chronic and/or acute), asthma, pulmonary arterial hypertension and chronic obstructive pulmonary disease (COPD). Cancers include adrenal, bladder, cervical, colon, esophageal, gallbladder, kidney, liver, lung, ovarian, pancreatic, prostatic, rectal, stomach, and uterine cancers. Body tissues include renal arteries, vascular lumen, nonvascular lumen, pulmonary artery, airway, sinus, esophagus, respiratory lumens, digestive lumens, cancers, tumors, and urological lumens. The energy can in some embodiments enhance the effect by accelerating reaction rate of the formulation and the nerves. The energy can be one of radiofrequency, cryoablation, microwave, laser, ultrasound, and high-intensity focused ultrasound energies. The energy delivery catheter can therefore be one of radiofrequency, cryoablation, microwave, laser, ultrasound, and high-intensity focused ultrasound catheters. Example formulations include gases, vapors, liquids, solutions, emulsion, and suspensions of one or more ingredients. If the formulation is vapors of one or more ingredients, the heat can be generated by condensation of the vapors into liquids in the tissue. If the formulation is liquids or solutions, the heat can be transferred by the high temperature formulations above body temperature. The desired temperature of the formulation can be in the range of −40 to 140° C., preferable in the range of −30 to 100° C., most preferable in the range of −20 to 80° C. The temperature of the treated tissue adjacent to the nerves can be lower than the desired temperature of the formulation and higher than that of the body temperature. The temperature of the treated tissue adjacent to the nerves can be in the range of −40 to 100° C., preferable in the range of −30 to 90° C., most preferable in the range of −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the formulation is a mixture of ethanol and water. The ethanol content of ethanol can be in the range of 10-100% by weight. The formulation can be delivered to the tissues of body lumen as vapors or liquid at desired temperature. The desired temperature of the vapor or liquid formulation can be in the range of −40 to 150° C., preferably in the range of −30 to 100° C., most preferably in the range of −20 to 80° C. The temperature of the tissue can be in the range of −40 to 90° C., preferably in the range of −30 to 80° C. The ethanol/water formulation can be a positive azeotrope. The azeotrope can be 95.63% ethanol and 4.37% water (by weight). Ethanol boils at 78.4° C., water boils at 100° C., but the azeotrope boils at 78.2° C., which is lower than either of its constituents. 78.2° C. is the minimum temperature at which any ethanol/water solution can boil at atmospheric pressure. The pressure of the mixture of ethanol and water infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the delivery catheter is a combination catheter of radiofrequency and infusion catheters. The radiofrequency catheters can be modified by reducing the electrode size (resulting in passive cooling via the blood flow) and/or cooling the electrode through active fluids, cooling either internally (closed-loop) or externally (open-loop). Cooling electrodes increases energy delivery into the nerve tissue. In some embodiments of externally cooling (open-loop), the chemical formulation can replace the active cooling fluids. The disclosed formulation can in some embodiments be used not only for cooling electrodes, but also for chemical ablation. The formulations can diffuse and permeate into the nerve tissue uniformly, and they can ablate the nerves in adventitia uniformly in the body lumen. Therefore, the chemical ablation formulation can be delivered during, before, and/or after the thermal ablations. The thermal ablations can involve radiofrequency, cryoablation, microwave, laser, ultrasound, and/or high-intensity focused ultrasound. Therefore, the methods can improve safety and efficacy of the treatments.

In some embodiments, the delivery catheter comprises infusion lumen, energy delivery lumen, guide wire lumen, inflation lumen, energy delivery port, formulation infusion port, and balloon inflation ports at the proximal end, energy releasing element, formulation releasing exit, and single or double balloons at distal end. The energy delivery element can be one of radiofrequency, cryoablation, microwave, laser, ultrasound, and high-intensity focused ultrasound. The energy generator can be connected to the energy delivery port. The energy generator can be one of radiofrequency, cryoablation, microwave, laser, ultrasound, and high-intensity focused ultrasound energy generators. The balloon inflation port can be connected to inflation device. The formulation resource can be connected to the formulation infusion port at the proximal end of the delivery catheters.

In some embodiments, the formulation is a mixture of vapors comprising water, ethanol and oxygen. In another embodiment, the formulation is a mixture of vapors comprising water, ethanol and air. In some embodiments, the formulation is a mixture of vapors comprising water, ethanol, oxygen and nitrogen. These formulations with oxygen or air are especially useful for treatments of asthma and COPD.

In some embodiments, the formulation is a mixture of vapors comprising water, ethanol and iodine, wherein iodine vapor has effective amount to image the mixture of vapors in the wall of the body lumen. In some embodiments, the formulation is a mixture of liquids comprising water, ethanol and a surfactant. In some embodiments, the formulation is a mixture of liquids comprising water, ethanol and a contrast agent, wherein the contrast agent has effective amount to track the mixture in the wall of the body lumen by X-ray. The contrast agent can be one or more of iodine, ethyl iodide, sodium iodide, lipiodol, nonoxynol iodine, iobitridol, iohexol, iomeprol, iopamidol, iopentol, iopromide, ioversol, ioxilan, iotrolan, iodixanol, ioxaglate, and their derivatives. The content of the contrast agent in the formulation can be in the range of 2 to 20% by weight, preferably 5 to 15% by weight.

In some embodiments, the formulation is a mixture of acetic acid and water. The acetic acid content of the formulation can be in the range of 1-100% by weight, preferably 10-75% by weight, most preferable 20-50% by weight. The formulation can be delivered to the tissues of body lumen as vapors or liquid at desired temperature. The desired temperature of the vapor or liquid formulation can be in the range of −40 to 100° C., preferably in the range of −30 to 100° C., most preferably in the range of −30 to 80° C. The temperature of the tissue can be in the range of −30 to 80° C., preferably in the range 60 to 80° C. or −40 to −20° C. The temperature of the tissue can be in the range of −40 to 0° C., preferably in the range −30 to −20° C. The pressure of the mixture of acetic acid and water infused is higher than body lumen pressure (1 ATM). The pressure range of the formulation infused to the target tissue is from 1 to 12 ATM, or 1 to 8 ATM or 1 to 5 ATM, preferred 1 to 3 ATM. The acetic acid content in the formulation can be from 2% to 75% (by weight), preferably from 10% to 60% (by weight).

In some embodiments, the formulation is a mixture of liquids comprising water, acetic acid and a contrast agent, such as sodium iodide and lipiodol, wherein the contrast agent has effective amount to image the mixture of vapors in the wall of the body lumen. The acetic acid content of the formulation can be in the range of 1-100% by weight, preferably 10-75% by weight, most preferably 30-60% by weight. In another embodiment, the formulation is a mixture of liquids comprising water, acetic acid and a surfactant. The acetic acid content of the formulation can be in the range of 1-100% by weight, preferably 10-75% by weight, most preferably 30-60% by weight. In another embodiment, the formulation is a mixture of liquids comprising water, acetic acid and a contrast agent, wherein the contrast agent has effective amount to track the mixture in the wall of the body lumen by X-ray. The contrast agent can be one of iodine, ethyl iodide, sodium iodide, lipiodol, nonoxynol iodine, iobitridol, iohexol, iomeprol, iopamidol, iopentol, iopromide, ioversol, ioxilan, iotrolan, iodixanol, ioxaglate, and their derivatives. The content of the contrast agent in the formulation can be in the range of 2 to 20% by weight, preferably 5 to 15% by weight.

In some embodiments, the formulation is a mixture of liquids comprising ethanol and lipiodol (LIPIODOL ULTRA-FLUIDE), wherein the lipiodol has effective amount to image the mixture of vapors in the wall of the body lumen and also to injury the target nerve tissue. The lipiodol content of the formulation can be in the range of 10-80% by weight, preferably 15-75% by weight, most preferably 20-50% by weight. In another embodiment, the formulation is a mixture of liquids comprising water and lipiodol. The lipiodol content of the formulation can be in the range of 10-80% by weight, preferably 15-75% by weight, most preferably 20-50% by weight. In another embodiment, the formulation is a mixture of liquids comprising acetic acid and lipiodol. The content of the lipiodol in the formulation can be in the range of 10-80% by weight, preferably 15-75% by weight, most preferably 20-50% by weight.

In some embodiments, the formulation is a solution of phenol, water, and amount of a contrast agent, such as iodine, sodium iodide, lipiodol and iopromide. The phenol content can be in the range of 2-20% by weight, preferably 5-16% by weight. The formulation can be delivered to the tissues of body lumen as a solution at desired temperature. The desired temperature of the liquid formulation can be in the range of 0-100° C., preferably 20-95° C., most preferably 50-90° C. The temperature of the tissue can be in the range of 36-80° C., preferably 60-80° C. The phenol can be an effective agent for ablation. The pressure of the solution infused is higher than body lumen pressure (1 ATM). The pressure range of the solution infused to the target tissue is from 1 to 12 ATM, or 1 to 8 ATM or 1 to 5 ATM, preferred 1 to 3 ATM.

In some embodiments, the formulation is a solution of ethylene glycol, water, and a small amount of a contrast agent, such as iodine and iopromide. The ethylene glycol content can be in the range of 2-90% by weight, preferably 15-75% by weight. The desired temperature of the liquid formulation can be in the range of 20-150° C., preferably of 40-120° C., most preferably of 60-90° C. The pressure of the solution infused is higher than body lumen pressure (1 ATM). The pressure range of the solution infused to the target tissue is from 1 to 12 ATM, or 1 to 8 ATM or 1 to 5 ATM, preferred 1 to 3 ATM.

In some embodiments, the formulation is a solution of glycerol, water, and a small amount of a contrast agent, such as iodine and iopromide. The glycerol content can be in the range of 2-90% by weight, preferably 15-75% by weight. The desired temperature of the liquid formulation can be in the range of 20-150° C., preferably 40-120° C., most preferably 60-90° C. The pressure of the solution infused is higher than body lumen pressure (1 ATM). The pressure range of the solution infused to the target tissue is from 1 to 12 ATM, or 1 to 8 ATM or 1 to 5 ATM, preferred 1 to 3 ATM.

In some embodiments, the formulation is a mixture of propanol and water. The propanol content of ethanol can be in the range of 10-99% by weight. The formulation can be delivered to the nerves of body lumen as vapors or liquid at desired temperature. The desired temperature of the vapor or liquid formulation can be in the range of 20-100° C., preferably 40-95° C., most preferably 60-90° C. The temperature of the nerve tissue can be in the range of 36-80° C., preferably 60-80° C. The propanol/water formulation can be an azeotrope. The azeotrope can be 71.7% propanol and 28.3% water (by weight). Propanol boils at 97.2° C., water boils at 100° C., but the azeotrope boils at 87.7° C., which is lower than either of its constituents. The pressure of the solution infused is higher than body lumen pressure (1 ATM). The pressure range of the solution infused to the target tissue is from 1 to 12 ATM, or 1 to 8 ATM or 1 to 5 ATM, preferred 1 to 3 ATM.

In some embodiments, the formulation is a mixture of isopropanol and water. The isopropanol content can be in the range of 10-99% by weight. The formulation can be delivered to the nerves of body lumen as vapors or liquid at desired temperature. The desired temperature of the vapor or liquid formulation can be in the range of 20-100° C., preferably 40-95° C., most preferably 60-90° C. The temperature of the nerve tissue can be in the range of 20-80° C., preferably 60-80° C. The isopropanol/water formulation can be an azeotrope. The azeotrope can be 87.9% propanol and 12.1% water (by weight). Isopropanol boils at 82.5° C., water boils at 100° C., but the azeotrope boils at 80.4° C., which is lower than either of its constituents. The pressure of the solution infused is higher than body lumen pressure (1 ATM). The pressure range of the solution infused to the target tissue is from 1 to 12 ATM, or 1 to 8 ATM or 1 to 5 ATM, preferred 1 to 3 ATM.

In some embodiments, the formulation is a mixture of ethanol and ethyl acetate. The content of ethyl acetate can be in the range of 10-99% by weight. The formulation can be delivered to the tissues of human body as vapors or liquid at desired temperature. The desired temperature of the vapor or liquid formulation can be in the range of 20-100° C., preferably 40-95° C., most preferably 60-90° C. The temperature of the tissue can be in the range of 36-80° C., preferably 60-80° C. The ethyl acetate/ethanol formulation can be an azeotrope. The azeotrope can be 69.7% ethyl acetate and 30.3% ethanol (by weight). Ethyl acetate boils at 77.1° C., ethanol boils at 78.4° C., but the azeotrope boils at 71.8° C., which is lower than either of its constituents. The pressure of the solution infused is higher than body lumen pressure (1 ATM). The pressure range of the solution infused to the target tissue is from 1 to 12 ATM, or 1 to 8 ATM or 1 to 5 ATM, preferred 1 to 3 ATM.

In some embodiments, the formulation is a mixture of ethanol and ethyl iodide. The content of ethyl iodide can be in the range of 10-99% by weight. The formulation can be delivered to the nerves of body lumen as vapors or liquid at desired temperature. The desired temperature of the vapor or liquid formulation can be in the range of 20-100° C., preferably 40-95° C., most preferably 60-90° C. The temperature of the tissue can be in the range of 36-80° C., preferably 60-80° C. The ethyl iodide/ethanol formulation can be an azeotrope. The azeotrope can be 87% ethyl iodide and 13% ethanol (by weight). Ethyl iodide boils at 72.3° C., ethanol boils at 78.4° C., but the azeotrope boils at 63° C., which is lower than either of its constituents. The pressure of the solution infused is higher than body lumen pressure (1

ATM). The pressure range of the solution infused to the target tissue is from 1 to 12 ATM, or 1 to 8 ATM or 1 to 5 ATM, preferred 1 to 3 ATM.

In some embodiments, the formulation is a mixture of water, ethanol, and ethyl acetate. The content of ethanol can be in the range of 2-99% by weight. The content of ethyl acetate can be in the range of 2-85% by weight. The formulation can be delivered to the tissues of human body as vapors or liquid at desired temperature. The desired temperature of the vapor or liquid formulation can be in the range of 20-100° C., preferably 40-95° C., most preferably 60-90° C. The temperature of the tissue can be in the range of 36-80° C., preferably 60-80° C. The ethyl acetate/ethanol formulation can be an azeotrope. The azeotrope can be a mixture of 7.8% water, 83.2% ethyl acetate, and 9.0% ethanol by weight. Ethyl acetate boils at 77.1° C., ethanol boils at 78.4° C. and water boils at 100° C., but the azeotrope boils at 70.3° C., which is lower than any of its constituents. The pressure of the solution infused is higher than body lumen pressure (1 ATM). The pressure range of the solution infused to the target tissue is from 1 to 12 ATM, or 1 to 8 ATM or 1 to 5 ATM, preferred 1 to 3 ATM.

In some embodiments, a delivery catheter is used to infuse the formulation to tissues of a human body. The delivery catheter can be a needle or needle-based catheter, e.g., under guidance of ultrasound imaging. The delivery catheter can be a balloon based catheter. The balloon based catheters can have at least one or two balloons, e.g., comprise single or double balloons. The delivery catheter can be an infusion catheter. The combination of balloon catheter and infusion catheter can be used as well in the procedure.

Referring now to the figures, FIG. 1 shows a delivery catheter 10 having an elongated shaft 11 with at least one inner lumen, a distal end 13, and a proximal end 14. At the distal end 13 are proximal 20 and distal 21 lumen-conforming balloons. In any configuration, the tubing of the catheter shaft 11 may be extruded from plastic materials, e.g. thermoplastics, polyimides, polyetherimides, polyethylenes, polyurethanes, polyesters, polyamide, Pebax, nylon, fluorinated polyurethane, polyether ether ketone, polysulfone, or the like. The catheter shaft 11 may be extruded or formed having a variety of lumen cross-sections, including circular or elliptic lumens. Further, as shown in FIG. 1, the catheter 10 may be equipped with a distal balloon inflation port 40 for the inflation of the distal balloon 21 and a proximal balloon inflation port 41 for inflation of the proximal balloon 20, rendering the proximal 20 and distal 21 balloons separately inflatable. Lumen-conforming balloons are balloons that can be inflated at a pressure less than that to deform the lumen wall. The balloon material is selected to be flexible and usable at high temperature, such that the balloon, when inflated, is compliant. In some embodiments, the balloon material is one of polyamides, nylons, Pebax, polyesters, polyethylene teraphthalate, and their copolymers. The diameter of the balloons can range from about 2 millimeters to about 30 millimeters, dependent on the diameter of the treatment site. In some embodiments, the diameter of each balloon is about 2 millimeters ("mm"). Alternatively, the diameter of each balloon can be about 3 millimeters, or alternatively about 4 millimeters, or alternatively about 5 millimeters, or alternatively about 6 millimeters, or alternatively about 7 millimeters, or alternatively about 8 millimeters, or alternatively about 9 millimeters, or alternatively about 10 millimeters, or alternatively about 12 millimeters, or alternatively about 15 millimeters, or alternatively about 20 millimeters, or alternatively about 25 millimeters, or alternatively about 30 millimeters.

In some embodiments, the catheter is electrode free. In particular, the catheter can be free of any sources of ablative energy, such as radiofrequency, ultrasound, microwave energy.

In some embodiments, at least one marker band 22b is located proximally to the proximal balloon 20 and at least one marker band 23a is located distally to the distal balloon 21. The balloon catheter may be a rapid exchange or over-the-wire catheter and made of any suitable biocompatible material. The material of balloon 20 and 21 can be made of one of polyesters, polyamides, nylon 12, nylon 11, polyamide 12, block copolymers of polyether and polyamide, Pebax, polyurethanes, and block copolymers of polyether and polyester. The diameter of balloon 21 can be equal or less than that of balloon 20.

Figure 2A:
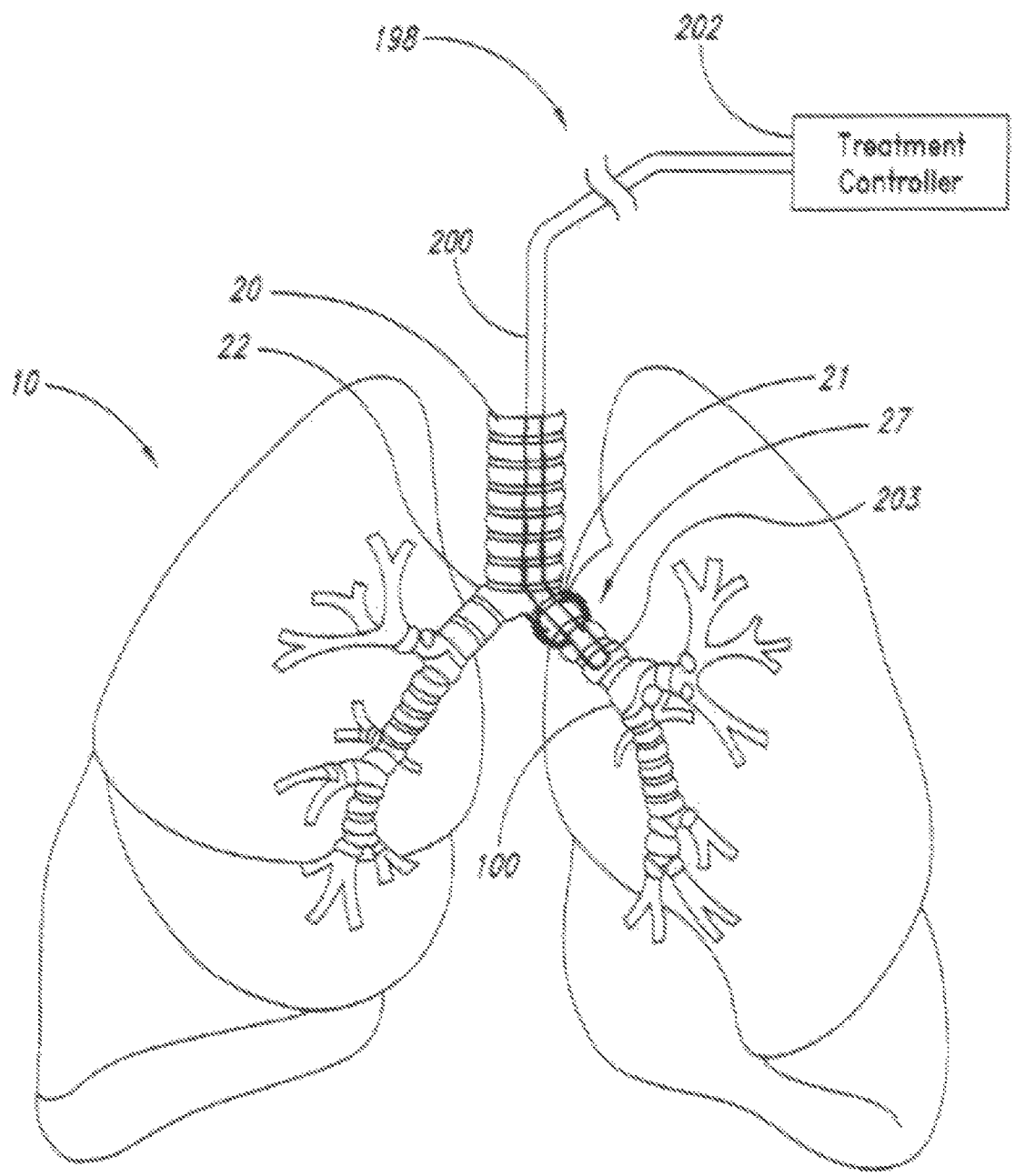
FIG. 2A is an embodiment of formulation infusion to the airway with the single balloon delivery catheter.
Figure 2B:
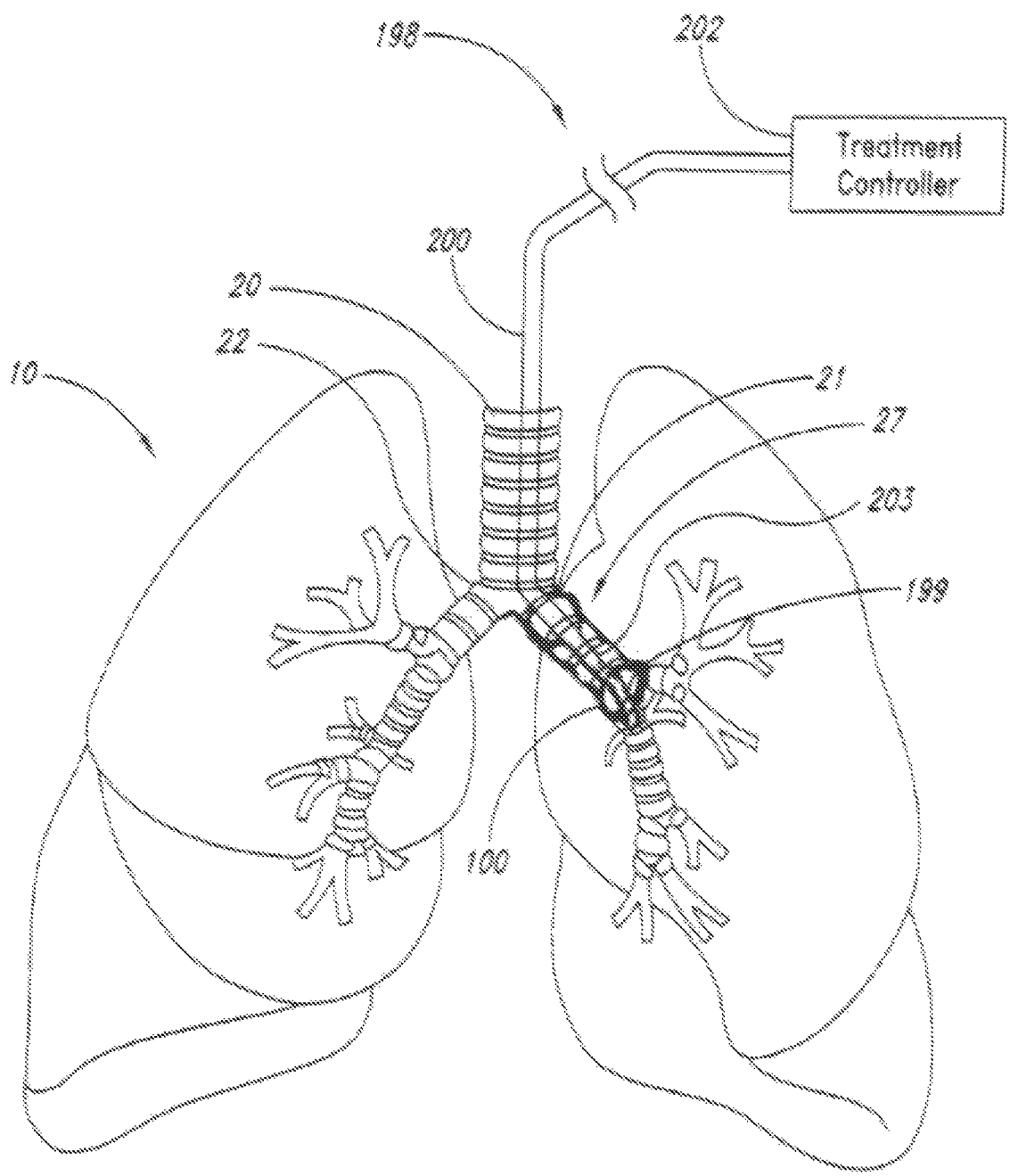
FIG. 2B is an embodiment of formulation infusion to the airway with the double balloon delivery catheter.

FIGS. 2A and 2B are schematic views of a balloon delivery catheter 198 positioned within a left main bronchus for treatments of asthma and COPD. The delivery catheter 198 of FIGS. 2A and 2B can treat airways that are distal to the main bronchi 21, 22. For example, the delivery catheter 198 can be positioned in higher generation airways (e.g., airway generations >2) to affect remote distal portions of the bronchial tree 27. The delivery system 198 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

The delivery catheter 198 can also be used in segmental or subsegmental bronchi. Each segmental bronchus may be treated by delivering the formulation to a single treatment site along each segmental bronchus. For example, the formulation can be delivered to each segmental bronchus of the right lung. In some procedures, one or two applications of the formulation can treat most of or substantially the entire right lung. In some procedures, most or substantially all of both lungs are treated using less than two to six different applications. Depending on the anatomical structure of the bronchial tree, segmental bronchi can often be denervated using one or two applications.

The delivery catheter 198 can affect nerve tissue while maintaining function of other tissue or anatomical features, such as the mucous glands, cilia, smooth muscle, body lumens (e.g., blood vessels), and the like. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, the delivery catheter 198 is capable of denervating a portion of an airway of the bronchial tree 27 to attenuate one or more nervous system signals transmitted by nerve tissue. Denervating can include damaging all of the nerve tissue of a section of a nerve trunk along an airway to stop substantially all of the signals from traveling through the damaged section of the nerve trunk to more distal locations along the bronchial tree. If a plurality of nerve trunks extends along the airway, each nerve trunk can be damaged. As such, the nerve supply along a section of the bronchial tree can be cut off. When the signals are cut off, the distal airway smooth muscle can relax leading to airway dilation. This airway dilation reduces airflow resistance so as to increase gas exchange in the lungs, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If the formulation at the desired temperature is used to destroy the nerve tissue outside of the airways, a therapeutically effective amount of the formulation does not reach a significant portion of the non-targeted smooth muscle tissue.

As shown in FIGS. 2A and 2B, the delivery system 198 can include a treatment controller 202 and an intraluminal elongate assembly 200 connected to the controller 202. The elongate assembly 200 can be inserted into the trachea 20 and navigated into and through the bronchial tree 27 with or without utilizing a delivery assembly. The elongate assembly 200 can include a distal tip 203 capable of selectively affecting tissue.

The controller 202 of FIG. 2A can include one or more processors, microprocessors, digital signal processors (DSPs), field programmable gate arrays (FPGA), and/or application-specific integrated circuits (ASICs), memory devices, buses, power sources, pump, formulation resources, vapor resources, liquid resources, contrast resources, vapor generator, desired temperature formulation generator, and the like.

The distal tip 203 of FIGS. 2A-2B can target various sites in the lungs 10, including, without limitation, nerve tissue, fibrous tissue, diseased or abnormal tissues, muscle tissue, blood, blood vessels, anatomical features (e.g., membranes, glands, cilia, and the like), or other sites of interest.

Figure 2C:
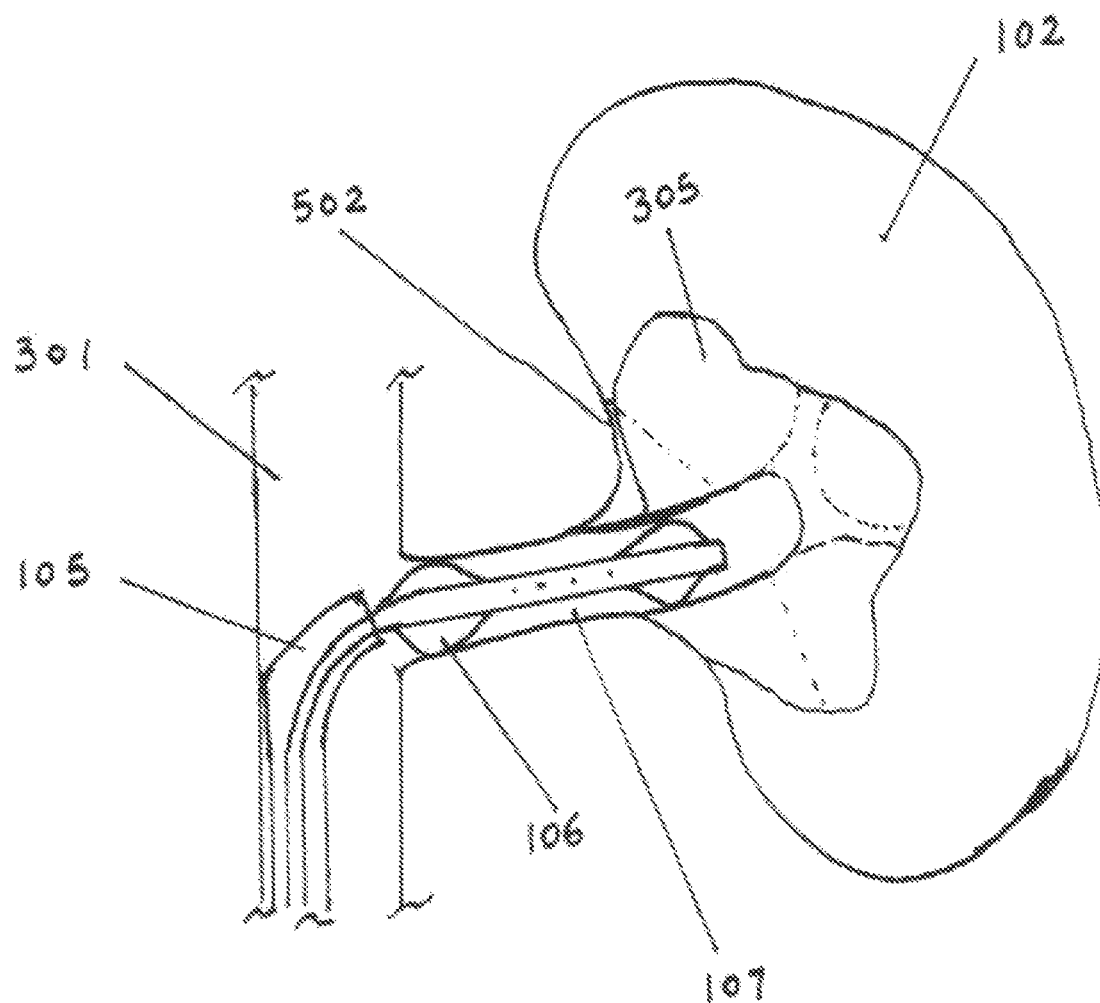
FIG. 2C is an embodiment of formulation infusion to the renal artery with the double balloon delivery catheter.

FIG. 2C is a schematic view of a double balloon delivery catheter positioned within a renal artery. The delivery catheter 106 of FIG. 2C can be used to treat hypertension. The formulation can be infused to the wall of the renal arteries adjacent to renal nerves for denervation. Some of the elements of the renal vascular system are omitted in FIG. 2C.

Figure 3:
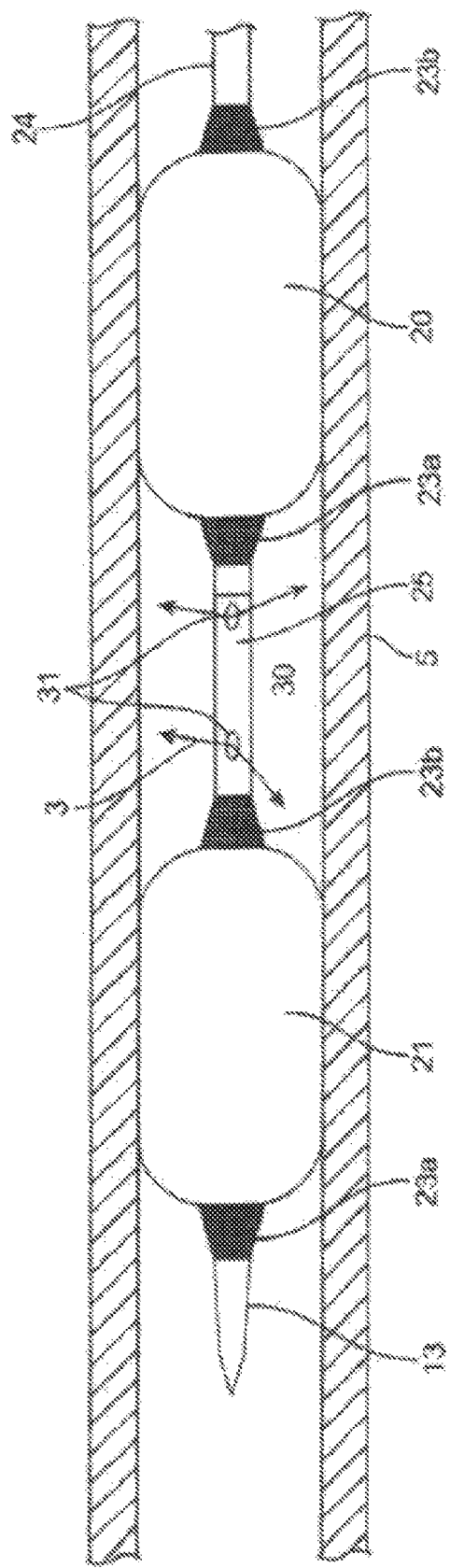
FIG. 3 is an embodiment of a partial cross-sectional view of the double balloon delivery catheter in a body lumen.

In some embodiments, the catheter 10 disclosed herein allows for the formulation to be substantially homogeneous throughout the treatment window 30 as shown in FIG. 3. The position, diameter, number, and frequency of lateral apertures 31 can result in the substantially homogeneous filling of the treatment window 30. FIG. 3 depicts a catheter positioned in a body lumen 5 having two lateral apertures 31 located within the treatment window 30 for the delivery of the therapeutic agent 3. The lateral apertures 31 as shown in FIG. 3 are in fluid communication with the inner lumen 25. Lateral apertures 31 located within the treatment window 30 can be in communication with either the outer 24 or inner 25 lumen such that the formulation is delivered homogeneously to the treatment window 30.

Figure 4:
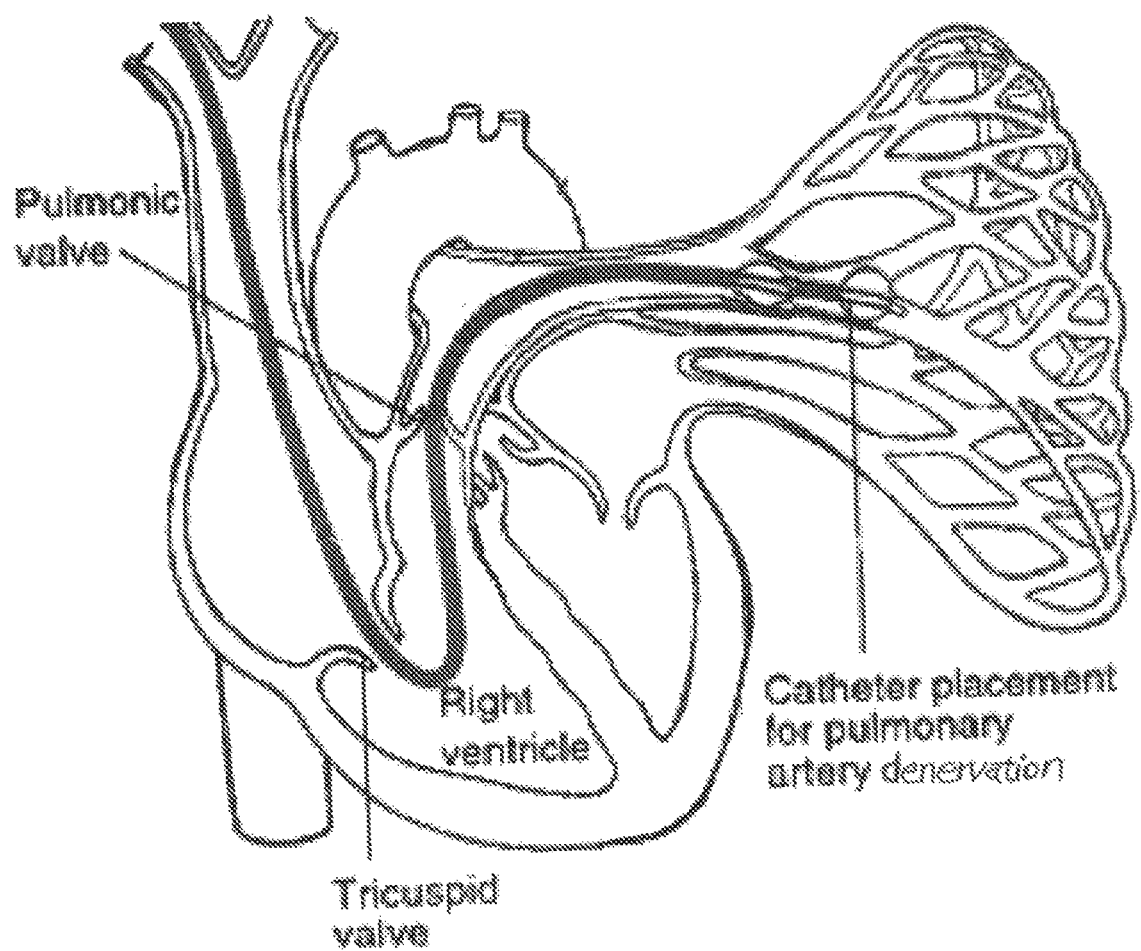
FIG. 4 is an embodiment of formulation infusion to pulmonary artery with the double balloon delivery catheters.

FIG. 4 is a schematic view of a double balloon delivery catheter positioned within a pulmonary artery. The delivery catheter of FIG. 4 can be used to treat pulmonary hypertension. The formulation can be infused to the wall of the pulmonary arteries adjacent to nerves for denervation. The front balloon of the depicted delivery catheter is located at the bifurcation. A baseline pulmonary artery angiography can be performed to identify the pulmonary artery bifurcation level and calculate the artery diameter. An 8F long sheath is shown inserted through the femoral vein and advanced to the main pulmonary artery. The double balloon catheter is advanced along the long shealth. The front balloon is positioned at the bifurcation. The nerves near bifurcation are injured by ablation from the formulation infused by the delivery catheter.

Some embodiments of the invention also include the step of delivering the formulation, such as vapor or liquid to the segment of the body lumen at the delivery rate and for the determined duration. The formulation may be heated to at least 80° C., or at least 100° C., or at least 150° C. before delivering the formulations. The delivery catheters, including the balloon and shafts, are functional when the formulations are at temperatures of at least 80° C., 100° C., or 150° C. The materials in the balloon and shafts of the catheters will sustain these high temperatures. In some embodiments, delivering the vapor causes the vapor to change to liquid, and the energy released during the phase change is transferred to the tissue of the segment or sub-segment.

In some embodiments, the safe and efficacious dosage for treating the tissue is between about 2 cal/g and about 150 cal/g., preferably between about 5 cal/g and about 100 cal/g., and the energy flow rate of the delivery system is between about 2 calories/second and about 500 calories/second, preferable between about 5 cal/g and about 150 cal/g. In some embodiments, the generator can create a formulation, such as vapors or liquids, having a pressure between about 1 to 12 ATM psi at a temperature between about 20-150° C., preferable about 50-120° C.

Depending on the desired degree of injury for the tissues, a safe and efficacious amount of the formulation and/or energy, or dose of the formulation and/or energy (e.g., calories/gram), to be applied to the tissues can be determined to accomplish that result. In general, as the dose increases the degree of injury to the tissue increases. The desired degree of injury to the tissues can therefore be controlled by altering the dose of formulations such as vapors or liquids at desired temperature applied to the tissues.

To be effective, the energy dose in preferred embodiments varies from about 1 cal/g to about 100 cal/g and/or the dose of the formulation in some embodiments varies from 0.2 microliter to 200 milliliters. These limits are, however, not intended to be definitive limitations of the doses applied, as other delivery parameters described below (e.g., delivery rate, delivery duration, etc.) may allow different doses to be applied to accomplish the same or similar injury to the tissue.

After determining the dose to apply to the tissue, the amount of total energy or formulation that needs to be applied by a delivery system (such as the delivery system described in the invention) to the tissue can be determined. This is done generally by multiplying the dose (cal/g) by the amount of tissue to be treated (grams) to determine the amount of formulation (ml) and energy (cals) to deliver.

The delivery (or flow) rate, or the rate at which the delivery system delivers the formulation, generally determines the duration that the formulation will be delivered to generate the determined amount of energy. For example, to deliver 300 calories to a segment of the lung at a delivery rate of 30 cals/second, the treatment duration would be 10 seconds. The delivery rate is generally between about 2 cals/second to about 200 cals/second. Again, these limitations are not intended to be definitive limitations and the delivery rate may be higher or lower depending on other treatment and/or delivery parameters.

Treatment times can vary depending on the volume, mass to be treated, and the desired injury to the tissue. Treatment times can vary from about 2 seconds to about 60 minutes. In some embodiments for causing injury to relief symptoms, the safe and effective treatment time is between about 4 seconds and about 30 minutes.

The delivery rate can be set via controls of a delivery system. Once the user sets the delivery rate, the formulation resources can establish the requisite amount of pressure to deliver the vapor or liquid at the desired rate by adjusting the amount of pressure applied. Changing the delivery rate setting will cause the generator to adjust the amount of pressure in the generator. The pressure in the vapor generator can range from between about 5 psi to over about 200 psi, preferable between about 10 psi to over 50 psi.

In some embodiments, the method for treating hypertension includes inserting a delivery catheter percutaneously into the renal artery adjacent to nerves; infusing a formulation described herein wherein at a desired temperature to the tissue of the body lumen adjacent to the nerves, wherein amount of the formulation and/or heat delivered is effective to injure or damage the nerves to have a benefit, such as lower blood pressure; and withdrawing the delivery catheters from the body lumen. The heat can be used to enhance the effect by accelerating reaction rate of the formulation and the nerves. The formulations can comprise gases, vapors, liquids, solutions, emulsion, or suspensions of one or more ingredients. If the formulation comprises vapors of one or more ingredients, the heat can be generated by condensation of the vapors into liquids in the tissue. If the formulation is liquids or solutions, the heat can be transferred by the high temperature formulations above body temperature. The desired temperature of the formulation can be in the range of −40 to 140° C., preferably −30 to 100° C., most preferably −20 to 80° C. The temperature of the treated tissue adjacent to the nerves can be lower than the desired temperature of the formulation and higher than that of the body temperature. The temperature of the treated tissue adjacent to the nerves can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the method for treating pulmonary arterial hypertension includes performing a pulmonary artery (PA) angiography to identify the PA bifurcation level; inserting a delivery catheter percutaneously through the femoral vein into the pulmonary artery adjacent to nerves near PA bifurcation; locating the front balloon of the double balloon catheter at the bifurcation; infusing a formulation described herein at a desired temperature to the tissue of the body lumen adjacent to the nerves, wherein amount of formulation and/or heat delivered is effective to injure or damage the nerves to have a benefit, such as lower blood pressure; and withdrawing the delivery catheters from the body lumen. The heat can enhance the effect by accelerating reaction rate of the formulation and the nerves. The formulations can comprise gases, vapors, liquids, solutions, emulsion, or suspensions of one or more ingredients. If the formulation comprises vapors of one or more ingredients, the heat can be generated by condensation of the vapors into liquids in the tissue. If the formulation is liquids or solutions, the heat can be transferred by the high temperature formulations above body temperature. The desired temperature of the formulation can be in the range of −40 to 140° C., preferably −30 to 100° C., most preferably −20 to 80° C. The temperature of the treated tissue adjacent to the nerves can be lower than the desired temperature of the formulation and higher than that of the body temperature. The temperature of the treated tissue adjacent to the nerves can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the method for treating asthma includes inserting a delivery catheter into the airways adjacent to nerves; infusing a formulation described herein at desired temperature to the tissue of the airway adjacent to the nerves, wherein amount of the formulation and/or heat delivered is effective to injure or damage the nerves to have a benefit, such as relief of shortness of breath; and withdrawing the delivery catheters from the body lumen. The heat can enhance the effect by accelerating reaction rate of the formulation and the nerves. The formulations can comprise gases, vapors, liquids, solutions, emulsion, and suspensions of one or more ingredients. If the formulation comprises vapors of one or more ingredients, the heat can be generated by condensation of the vapors into liquids in the tissue. If the formulation comprises liquids or solutions, the heat can be transferred by the high temperature formulations above body temperature. The desired temperature of the liquid formulation can be in the range of −40 to 140° C., preferably −30 to 100° C. most preferably −20 to 80° C. The temperature of the treated tissue adjacent to the nerves can be lower than the desired temperature of the formulation and higher than that of the body temperature. The temperature of the treated tissue adjacent to the nerves can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the method for treating COPD includes inserting a delivery catheter into the airway adjacent to nerves, infusing a formulation described herein at desired temperature to the tissue of the body lumen adjacent to the nerves, wherein amount of the formulation and/or heat delivered is effective to injure or damage the nerves to have a benefit, such as relief of COPD symptoms, and withdrawing the delivery catheters from the airway. The heat can enhance the effect by accelerating reaction rate of the formulation and the nerves. The formulation can comprise gases, vapors, liquids, solutions, or suspensions of one or more formulations. If the formulation comprises vapors of one or more ingredients, the heat can be generated by condensation of the vapors into liquids. If the formulation comprises liquids or solutions, the heat can be transferred by the high temperature formulations above body temperature. The desired temperature of the formulation can be in the range of −40 to 140° C., preferably −30 to 100° C., most preferably −20 to 80° C. The temperature of the treated tissue adjacent to the nerves can be lower than the desired temperature of the formulation and higher than that of the body temperature. The temperature of the treated tissue adjacent to the nerves can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the method for treating obesity includes inserting a delivery catheter into the digestive lumen adjacent to nerves, infusing a formulation described herein at desired temperature to the tissue of the digestive lumen adjacent to the nerves, wherein amount of the formulation and/or heat delivered is effective to injure or damage the nerves to have a benefit, such as lower body weight, and withdrawing the delivery catheters from the digestive lumen. The heat can enhance the effect by accelerating reaction rate of the formulations and the nerves. The formulations can comprise gases, vapors, liquids, solutions, emulsion and suspensions of one or more ingredients. If the formulation comprises vapors of one or more ingredients, the heat can be generated by condensation of the vapors into liquids. If the formulation comprises liquids or solutions, the heat can be transferred by the high temperature formulation above body temperature. The desired temperature of the liquid formulation can be in the range of −40 to 140° C., preferably −30 to 100° C., most preferably −20 to 80° C. The temperature of the treated tissue adjacent to the nerves can be lower than the desired temperature of the formulation and higher than that of the body temperature. The temperature of the treated tissue adjacent to the nerves can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the method for treating urological diseases includes inserting a delivery catheter into the urological lumen adjacent to nerves, infusing a formulation described herein at desired temperature to the tissue of the urological lumen adjacent to the nerves, wherein amount of the formulation and/or heat delivered is effective to injure or damage the nerves to have a benefit, such as control of urine flowing, and withdrawing the delivery catheters from the urological lumen. The heat can enhance the effect by accelerating reaction rate of the formulation and the nerves. The formulations can comprise gases, vapors, liquids, solutions, emulsions, and suspensions of one or more ingredients. If the formulation comprises vapors of one or more ingredients, the heat can be generated by condensation of the vapors into liquids. If the formulation comprises liquids or solutions, the heat can be transferred by the high temperature formulation above body temperature. The desired temperature of the liquid formulation can be in the range of −40 to 140° C., preferably −30 to 100° C., most preferably −20 to 80° C. The temperature of the treated tissue adjacent to the nerves can be lower than the desired temperature of the formulation and higher than that of the body temperature. The temperature of the treated tissue adjacent to the nerves can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the method for treating cancers or tumors includes inserting a needle or needle based delivery catheter percutaneously into the cancers or tumors under image guidance; infusing a formulation described herein at desired temperature to the cancer tissues of the human body, wherein amount of the formulation and/or heat delivered is effective to injure or damage or eliminate the cancer tissues to have a therapeutic benefit, such as shrinking or eliminating tumors; and withdrawing the delivery catheters from the body. The image guidance can include ultrasound, X-ray, CT scan, NMR imaging, scopes, or a combination thereof. Example cancers include adrenal, bladder, cervical, colon, esophageal, gallbladder, kidney, liver, lung, ovarian, pancreatic, prostatic, rectal, stomach, and uterine cancers. The heat can be used to enhance the effect by accelerating reaction rate of the formulation and the cancer tissues. The formulations can comprise gases, vapors, liquids, solutions, emulsion and suspensions of one or more ingredients. If the formulation comprises vapors of one or more ingredients, the heat can be generated by condensation of the vapors into liquids. If the formulation comprises liquids or solutions, the heat can be transferred by the high temperature formulation above body temperature. The desired temperature of the formulation can be in the range of −40 to 140° C., preferably −30 to 100° C., most preferably −20 to 80° C. The temperature of the treated tissue can be lower than the desired temperature of the formulation and higher than that of the body temperature. The temperature of the treated tissue can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

In some embodiments, the method for treating pains includes inserting a needle or needle based delivery catheter percutaneously into the tissues with pains under image guidance; infusing a formulation described herein at desired temperature to the pain tissues, especially back pains and cancer pains, of the human body, wherein the amount of formulation and/or heat delivered is effective to injure or damage or eliminate the never tissues to have a therapeutic benefit, such as reducing or eliminating pains; and withdrawing the delivery catheters from the body. The image guidance can include ultrasound, X-ray, CT scan, NMR imaging, scopes, or a combination thereof. Example pains include head, arm, facial, lower limb, eye, jaw, scar, groin, adrenal, bladder, cervical, colon, esophageal, gallbladder, kidney, liver, lung, ovarian, pancreatic, prostatic, rectal, stomach, and uterine pains. The heat can be used to enhance the effect by accelerating reaction rate of the formulation and the pain tissues. The formulations can comprise gases, vapors, liquids, solutions, emulsion and suspensions of one or more ingredients. If the formulation comprises vapors of one or more ingredients, the heat can be generated by condensation of the vapors into liquids. If the formulation comprises liquids or solutions, the heat can be transferred by the high temperature formulation above body temperature. The desired temperature of the formulation can be in the range of −40 to 140° C., preferably −30 to 100° C., most preferably −20 to 80° C. The temperature of the treated tissue can be lower than the desired temperature of the formulation and higher than that of the body temperature. The temperature of the treated tissue can be in the range of −40 to 100° C., preferably −30 to 90° C., most preferably −20 to 80° C. The pressure of the formulation infused is higher than body lumen pressure (1 ATM). The pressure range of the formulation infused to the target tissue is from 1 to 12 ATM, or 1 to 8 ATM or 1 to 5 ATM, preferred 1 to 3 ATM.

What is claimed is:

1. A method of treating a disease, the method comprising:
    inserting a needle-based balloon delivery catheter into a vascular lumen adjacent to a nerve, wherein the needle-based balloon delivery catheter comprises a balloon disposed along an elongated shaft and the balloon has a diameter in an inflated state in a range of from 2 millimeters to 30 millimeters;
    inflating the balloon;
    infusing a chemical formulation at a temperature and at a pressure from the needle-based balloon delivery catheter adjacent to the nerve, wherein an amount of the chemical formulation delivered is effective to injure or damage the nerve to have a benefit of relieving symptoms of the disease, wherein the chemical formulation is at least one of 10 wt % to 100 wt % ethanol and 1 wt % to 100 wt % acetic acid;
    deflating the balloon; and
    withdrawing the needle-based balloon delivery catheter from the body lumen, wherein the chemical formulation interacts with the nerve resulting in denervation;
    wherein the disease is chosen from hypertension, diabetes, obesity, end-stage renal disease, heart failure, and a combination thereof.

2. The method of claim 1, wherein the chemical formulation comprises at least one of a gas, vapor, liquid, solution, and an emulsion and/or suspension of one or more ingredients.

3. The method of claim 1, wherein the temperature of the chemical formulation is in the range of −40° C. to 140° C.

4. The method of claim 1, wherein the pressure of the formulation is in the range of 1 to 12 ATM.

5. The method of claim 1, wherein the pressure of the chemical formulation is higher than the pressure of body lumen.

6. The method of claim 1, wherein the amount of the chemical formulation is in the range of 0.2 microliters to 200 milliliters.

7. The method of claim 1, wherein heat or energy is delivered from the chemical formulation adjacent to the nerve in an amount from about 2 cal/g to about 150 cal/g.

8. The method of claim 1, wherein the needle-based balloon delivery catheter is a balloon catheter, a double-balloon catheter, or a combination of a balloon catheter and an infusion catheter.

9. The method of claim 1, wherein the chemical formulation further comprises a therapeutic agent for nerve denervation, wherein the therapeutic agent is chosen from sodium channel blockers, tetrodotoxin, saxitoxin, decarbamoyl saxitoxin, vanilloids, neosaxitoxin, lidocaine, conotoxins, cardiac glycosides, digoxin, glutamate, staurosporine, amlodipine, verapamil, cymarin, digitoxin, proscillaridin, quabain, veratridine, domoic acid, oleandrin, carbamazepine, aflatoxin, guanethidine, guanethidine sulfate, and combinations thereof.

10. The method of claim 1, wherein the chemical formulation comprises a contrast agent for imaging nerve denervation.

11. The method of claim 1, wherein the method is a method of thermal and chemical ablation for treating a disease, wherein the infusing of the chemical formulation from the needle-based balloon delivery catheter adjacent to the nerve comprises delivering the chemical formulation and energy adjacent to the nerve, wherein the amount of energy and/or chemical formulation delivered is effective to injure or damage the nerve to relieve symptoms of the disease.

12. The method of claim 11, wherein the energy is chosen from radiofrequency, cryoablation, microwave, laser, ultrasound, high intensity focused ultrasound, vapor condensation of at least some of the chemical formulation to a liquid, and combinations thereof.

13. The method of claim 11, wherein the chemical formulation is infused to the nerve tissue during, before, or after the energy is delivered.

14. The method of claim 11, wherein the chemical formulation comprises water or saline, wherein infusion of the chemical formulation from the needle-based balloon delivery catheter adjacent to the nerve is effective to decrease the temperature of the vascular lumen adjacent to the nerve.

15. The method of claim 1, wherein the chemical formulation is 100% ethanol.

16. The method of claim 1, wherein the chemical formulation is an azeotrope of ethanol and water.

17. The method of claim 1, wherein the needle-based balloon delivery catheter further comprises a marker band located distally of the balloon.

18. The method of claim 1, wherein the balloon comprises a material chosen from a polyamide, a nylon, a polyether block amide, a polyester, a polyethylene terephthalate, a polyurethane, a copolymer thereof, and a mixture thereof.

19. A method of treating a disease, the method comprising:
    inserting a needle-based balloon delivery catheter into a vascular lumen adjacent to a nerve, wherein the needle-based balloon delivery catheter comprises a balloon disposed along an elongated shaft and the balloon has a diameter in an inflated state in a range of from 2 millimeters to 30 millimeters;
    inflating the balloon;
    infusing a chemical formulation at a temperature and at a pressure from the needle-based balloon delivery catheter adjacent to the nerve, and delivering heat and/or energy from the needle-based balloon delivery catheter adjacent to the nerve, wherein an amount of the heat and/or energy delivered combined with an amount of the chemical formulation delivered is effective to injure or damage the nerve resulting in denervation of the nerve and relief of symptoms of the treated disease, wherein the chemical formulation is at least one of 10 wt % to 100 wt % ethanol and 1 wt % to 100 wt % acetic acid;
    deflating the balloon; and
    withdrawing the needle-based balloon delivery catheter from the body lumen;
    wherein the disease is chosen from hypertension, diabetes, obesity, end-stage renal disease, heart failure, and a combination thereof.

20. The method of claim 19, wherein the heat and/or energy delivered adjacent to the nerve is sufficient to bring the temperature adjacent to the nerve to a range of −40° C. to 140° C.

21. The method of claim 19, wherein the heat and/or energy delivered adjacent to the nerve is in an amount from about 2 cal/g to about 150 cal/g.

22. The method of claim 19, wherein the energy is chosen from radiofrequency, cryoablation, microwave, laser, ultrasound, high intensity focused ultrasound, vapor condensation of at least some of the chemical formulation to a liquid, and combinations thereof.

23. The method of claim 19, wherein the needle-based balloon delivery catheter further comprises a marker band located distally of the balloon.

24. The method of claim 19, wherein the balloon comprises a material chosen from a polyamide, a nylon, a polyether block amide, a polyester, a polyethylene terephthalate, a polyurethane, a copolymer thereof, and a mixture thereof.

25. The method of claim 19, further comprising infusing a chemical formulation comprising water or saline from the needle-based balloon delivery catheter adjacent to the nerve to decrease the temperature of the vascular lumen adjacent to the nerve.

* * * * *